(12) United States Patent
Kawai et al.

(10) Patent No.: US 11,455,722 B2
(45) Date of Patent: Sep. 27, 2022

(54) SYSTEM WITH ENDOSCOPE AND IMAGE SENSOR AND METHOD FOR PROCESSING MEDICAL IMAGES

(71) Applicant: Sony Corporation, Tokyo (JP)

(72) Inventors: Takashi Kawai, Tokyo (JP); Kiyoshi Hosono, Tokyo (JP)

(73) Assignee: SONY CORPORATION, Tokyo (JP)

( * ) Notice: Subject to any disclaimer, the term of this patent is extended or adjusted under 35 U.S.C. 154(b) by 80 days.

(21) Appl. No.: 16/979,882

(22) PCT Filed: Mar. 12, 2019

(86) PCT No.: PCT/JP2019/009853
§ 371 (c)(1),
(2) Date: Sep. 11, 2020

(87) PCT Pub. No.: WO2019/181629
PCT Pub. Date: Sep. 26, 2019

(65) Prior Publication Data
US 2021/0019884 A1    Jan. 21, 2021

(30) Foreign Application Priority Data
Mar. 20, 2018   (JP) .............................. JP2018-051955

(51) Int. Cl.
*G06T 7/90* (2017.01)
*G06T 7/00* (2017.01)
(Continued)

(52) U.S. Cl.
CPC ........ *G06T 7/0012* (2013.01); *A61B 1/00096* (2013.01); *A61B 1/00188* (2013.01);
(Continued)

(58) Field of Classification Search
CPC ............... G06T 7/0012; G06T 7/80; G06T 2207/10068; G06T 2207/30168;
(Continued)

(56) References Cited

U.S. PATENT DOCUMENTS 6,831,693 B1 * 12/2004 Sunaga .............. G02B 17/0848
                                                      359/857
2009/0046196 A1    2/2009 Lavrentiev et al.
(Continued)

FOREIGN PATENT DOCUMENTS

JP    2015123293 A    7/2015
JP    2015156937 A    9/2015
(Continued)

OTHER PUBLICATIONS

International Search Report and Written Opinion dated May 27, 2019 for PCT/JP2019/009853 filed on Mar. 12, 2019, 10 pages.

*Primary Examiner* — Howard D Brown, Jr.
(74) *Attorney, Agent, or Firm* — Xsensus LLP

(57) ABSTRACT

A system includes an endoscope including a scope and an image sensor. The image sensor is configured to capture medical image data that includes effective image portion data and a mechanical vignetting portion data, the mechanical vignetting portion data of the medical image data being generated due to mechanical vignetting caused by a difference in the image sensor which generates the medical image data and the scope. There is also circuitry configured to determine evaluation information from image data which is from the effective image portion data, and execute a control process to at least partially control at least one of an autofocus processing, and an auto white balance processing on the endoscope on the basis of the evaluation information.

28 Claims, 20 Drawing Sheets

(51) Int. Cl.
*G06T 7/80* (2017.01)
*H04N 5/232* (2006.01)
*A61B 1/00* (2006.01)
*A61B 1/05* (2006.01)
*A61B 1/06* (2006.01)
*H04N 9/73* (2006.01)
*H04N 5/225* (2006.01)

(52) U.S. Cl.
CPC .............. *A61B 1/05* (2013.01); *A61B 1/0661* (2013.01); *G06T 7/80* (2017.01); *H04N 5/232123* (2018.08); *H04N 9/735* (2013.01); *G06T 2207/10068* (2013.01); *G06T 2207/30168* (2013.01); *H04N 2005/2255* (2013.01)

(58) Field of Classification Search
CPC .............. G06T 7/0002; A61B 1/00096; A61B 1/00188; A61B 1/05; A61B 1/0661; A61B 1/045; A61B 1/00009; H04N 5/232123; H04N 9/735; H04N 2005/2255; H04N 5/232
See application file for complete search history.

(56) References Cited

U.S. PATENT DOCUMENTS

| | | | |
|---|---|---|---|
| 2010/0048993 A1* | 2/2010 | Shidara | A61B 1/04 600/109 |
| 2011/0184236 A1 | 7/2011 | Yoshino | |
| 2014/0204187 A1* | 7/2014 | Sasaki | A61B 1/00174 348/65 |
| 2016/0227100 A1 | 8/2016 | Liu et al. | |
| 2017/0111624 A1* | 4/2017 | Jingu | A61B 1/00009 |
| 2018/0089855 A1* | 3/2018 | Rodrigues | G06T 7/90 |
| 2021/0019884 A1* | 1/2021 | Kawai | A61B 1/000095 |

FOREIGN PATENT DOCUMENTS

| | | |
|---|---|---|
| JP | 2017-170157 A | 9/2017 |
| WO | 2016088628 A1 | 6/2016 |
| WO | 2017/072950 A1 | 5/2017 |
| WO | 2017072853 A1 | 5/2017 |
| WO | 2017122349 A1 | 7/2017 |
| WO | 2017/145606 A1 | 8/2017 |
| WO | 2018/043550 A1 | 3/2018 |

* cited by examiner

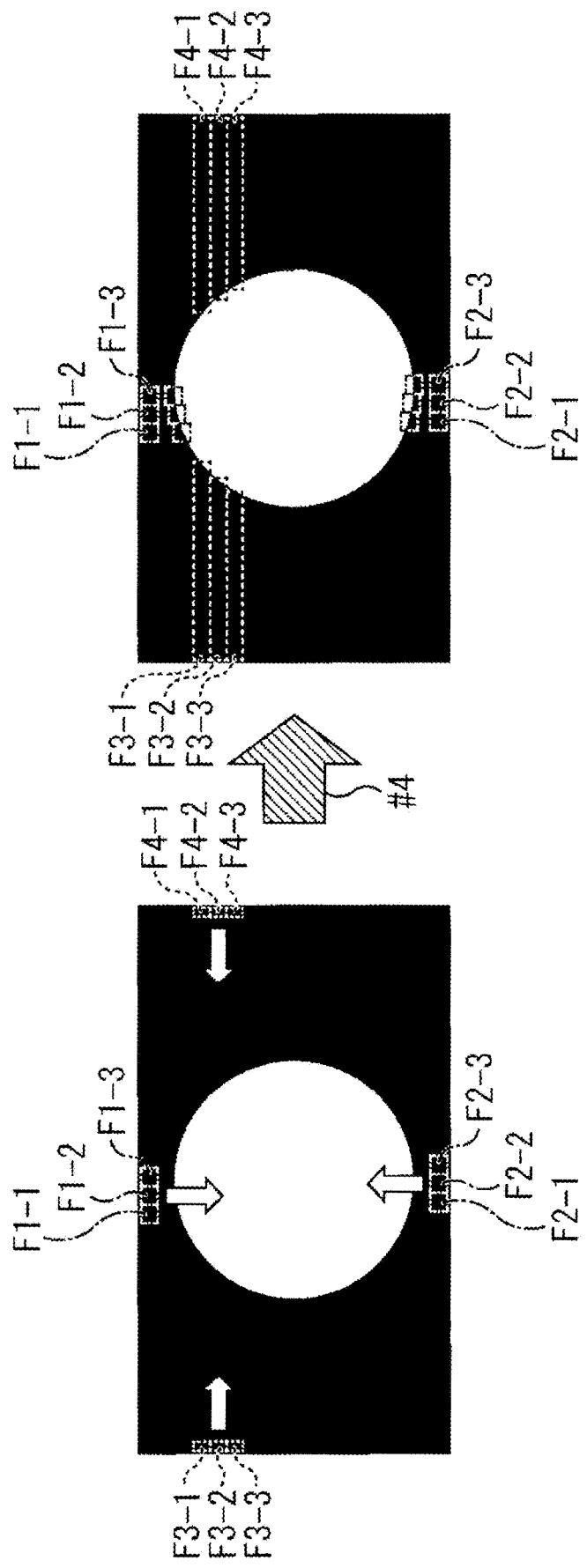

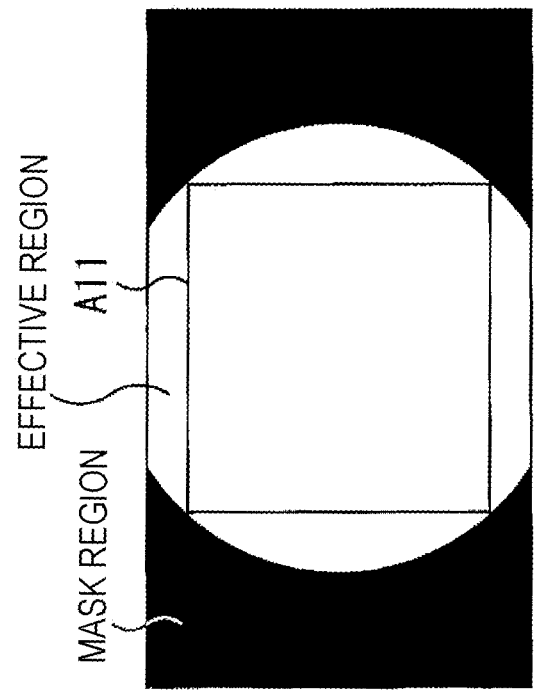
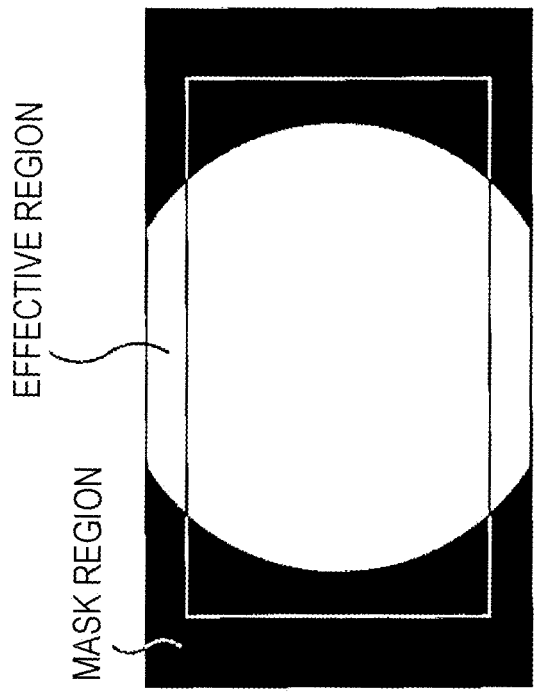
FIG. 18

FIG. 19
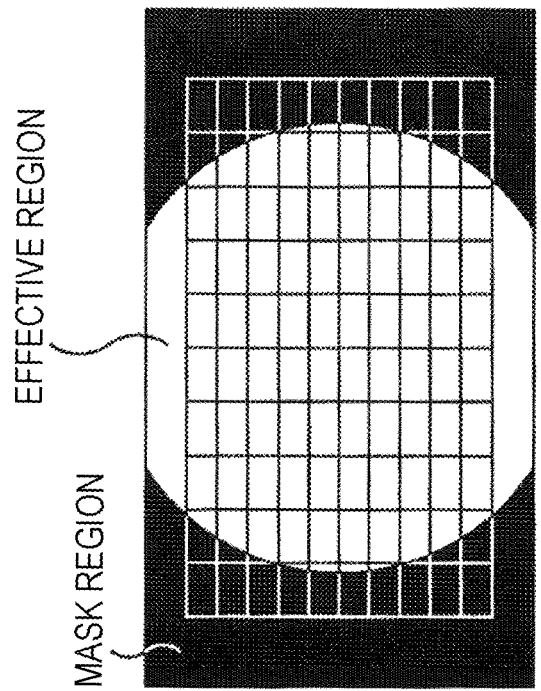
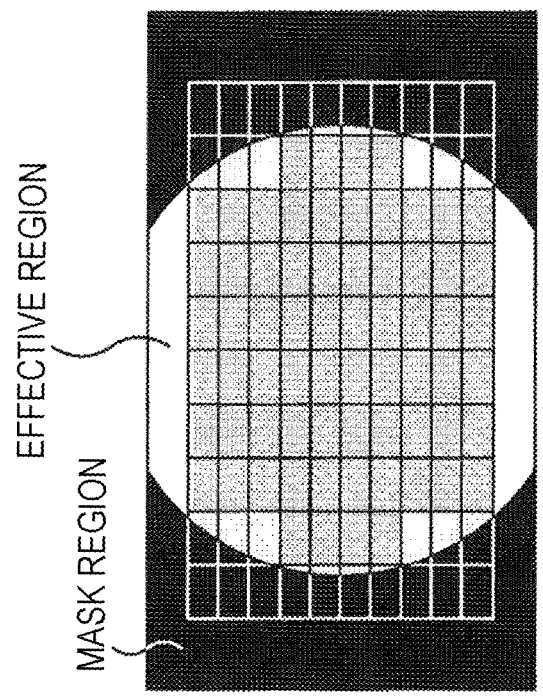

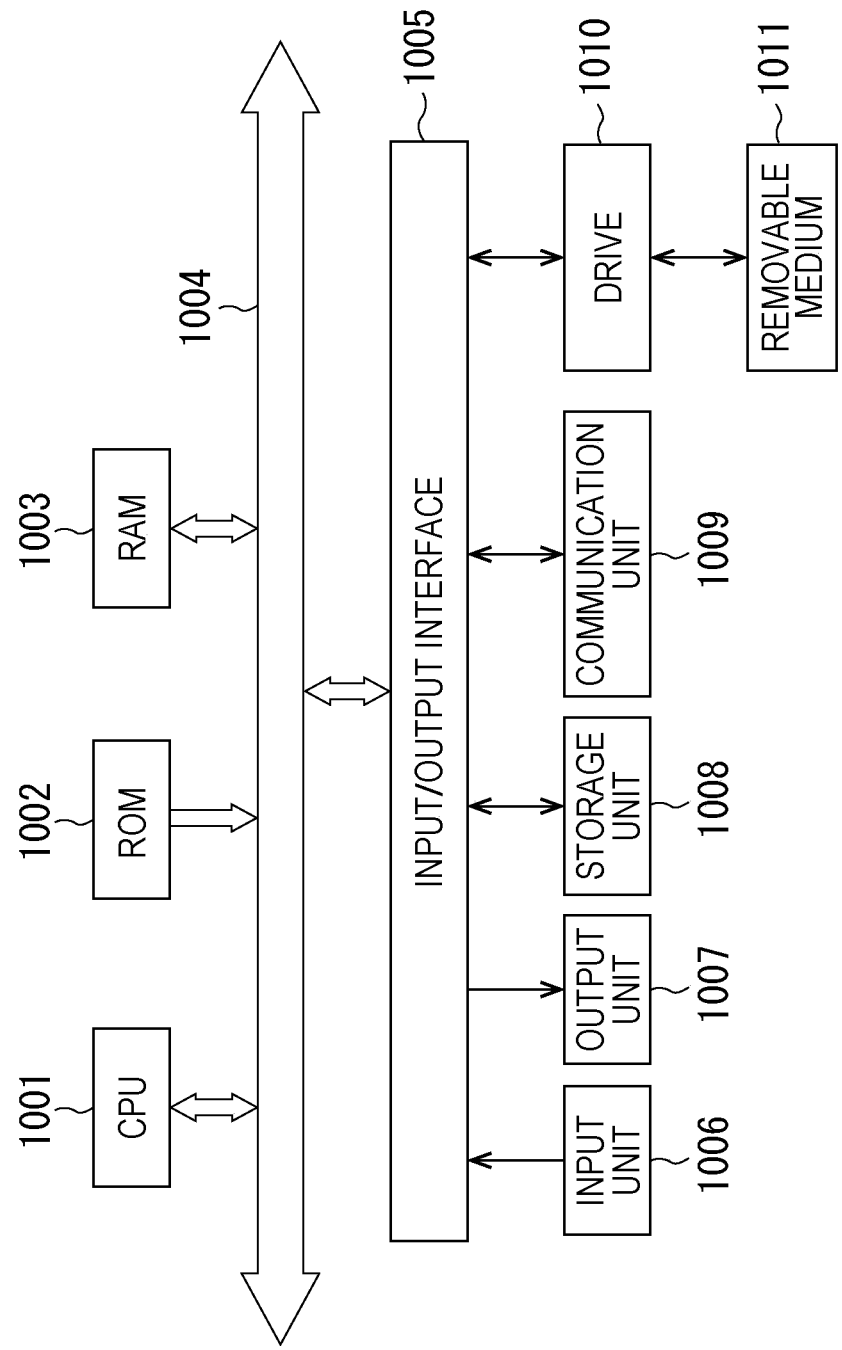

SYSTEM WITH ENDOSCOPE AND IMAGE SENSOR AND METHOD FOR PROCESSING MEDICAL IMAGES

CROSS-REFERENCE TO RELATED APPLICATIONS

The present application is based on PCT filing PCT/JP2019/009853, filed Mar. 12, 2019, which claims priority to JP 2018-051955, filed Mar. 20, 2018, the entire contents of each are incorporated herein by reference.

TECHNICAL FIELD

The present technology relates to an endoscope system, a control method, an information processing device, and a program, and more particularly, to an endoscope system, a control method, an information processing device, and a program capable of photographing an endoscopic image suitable for a surgical operation.

BACKGROUND ART

In recent years, an endoscopic surgical operation having low invasiveness has attracted attention. In order to obtain an endoscopic image suitable for the surgical operation, an endoscope having an autofocus (AF) function, an automatic exposure (AE) function, and an auto white balance (AWB) function has been proposed.

For example, PTL 1 discloses a technique of performing the AF function of the endoscope by calculating a focus evaluation value on the basis of the endoscopic image.

CITATION LIST

Patent Literature

PTL 1: JP 2013-80108A

SUMMARY OF INVENTION

Technical Problem

Typically, in the vicinity of a periphery of the endoscopic image, a mask region as a significantly dark area is generated due to an optical shadow of the scope (vignetting). For example, in a case where the AF is performed on the basis of such an endoscopic image, focusing may be performed on the mask region in some cases.

In addition, a position or size of the mask region changes depending on the type of the employed scope. Therefore, it is difficult to fix a calculation target region for the evaluation value in advance.

In view of the aforementioned circumstances, the present technology has been made to photograph an endoscopic image suitable for a surgical operation.

Solution to Problem

A system includes an endoscope including a scope and an image sensor. The image sensor is configured to capture medical image data that includes effective image portion data and a mechanical vignetting portion data, the mechanical vignetting portion data of the medical image data being generated due to mechanical vignetting caused by a difference in the image sensor which generates the medical image data and the scope. There is also circuitry configured to determine evaluation information from image data which is from the effective image portion data, and execute a control process to at least partially control at least one of an autofocus processing, and an auto white balance processing on the endoscope on the basis of the evaluation information.

Further, there is a method of processing medical image information which includes determining evaluation information using effective image portion data of medical image data, the medical image data including the effective image portion data and mechanical vignetting portion data, the mechanical vignetting portion data of the medical image data being generated due to mechanical vignetting caused by a difference in an image sensor which generates the medical image data and a medical instrument. Additionally, there is an executing of a control process including at least one of an autofocus process, or an auto white balance process on the basis of the evaluation information.

In the present technology, an effective region of the scope is detected from a photographic image photographed by the image sensing device, and a control process including at least one of an autofocus processing, an automatic exposure processing, or an auto white balance processing is executed on the basis of the evaluation value of the effective region.

Advantageous Effects of Invention

In the present technology, it is possible to photograph an endoscopic image suitable for a surgical operation. Moreover, the present technology permits a system which addresses issues with vignetting and provides advantageous focusing and/or white balance processing.

Note that the advantageous effects described herein are not necessarily limited, but may include any one of those described in this disclosure.

BRIEF DESCRIPTION OF DRAWINGS

FIG. 11 is a diagram illustrating further another exemplary setting of sampling frames in a case where a mask region is detected on the basis of the AF evaluation value.

FIG. 18 is a diagram illustrating an exemplary setting of the evaluation value calculation target region for the AE evaluation value.

FIG. 19 is a diagram illustrating another exemplary setting of the evaluation value calculation target region for the AE evaluation value.

FIG. 20 is a block diagram illustrating an exemplary configuration of a computer.

DESCRIPTION OF EMBODIMENTS

Embodiments of the present technology will now be described. The description will be made in the following sequence.

1. Configuration of Endoscope System
2. First Embodiment: Example of Detecting Mask Region on the basis of Sampling Value
3. Second Embodiment: Example of Detecting Mask Region on the basis of AF Evaluation Value
4. Third Embodiment: First Exemplary Setting of Evaluation Value Calculation Target Region
5. Fourth Embodiment: Second Exemplary Setting of Evaluation Value Calculation Target Region
6. Fifth Embodiment: Exemplary Autofocus processing
7. Operation of CCU
8. Other Examples <<Configuration of Endoscope System>>

Figure 1:
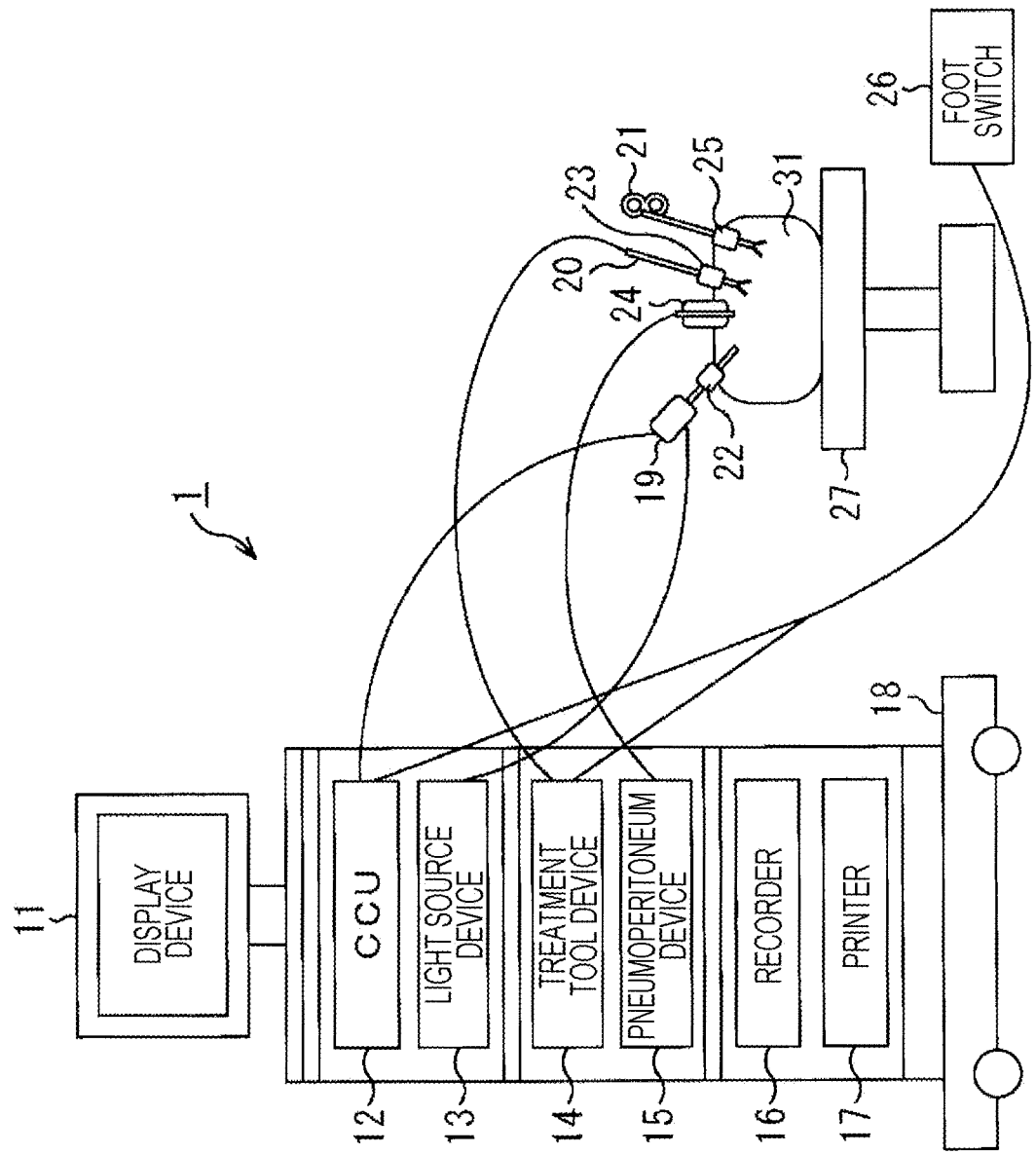
FIG. 1 is a diagram illustrating an exemplary configuration of an endoscope system according to an embodiment of the present technology.

FIG. 1 is a diagram illustrating an exemplary configuration of an endoscope system according to an embodiment of the present technology.

The endoscope system 1 of FIG. 1 includes a display device 11, a camera control unit (CCU) 12, a light source device 13, a treatment tool device 14, a pneumoperitoneum device 15, a recorder 16, and a printer 17 mounted on a cart 18.

In addition, the endoscope system 1 includes an endoscope 19, an energy treatment tool 20, a forceps 21, trocars 22 to 25, a foot switch 26, and a patient's bed 27. The endoscope system 1 is installed, for example, in a surgical operation room to assist an operator who performs a laparoscopic surgery for a lesion inside an abdomen 31 of a patient lying on the patient's bed 27.

The display device 11 includes a stationary two-dimensional display, a head-mount display, or the like. The display device 11 displays an image of a surgical treatment portion (surgical field area) supplied from the CCU 12 and the like.

The CCU 12 is connected to each part such as the light source device 13 and the endoscope 19. The CCU 12 receives the photographic image of the surgical treatment portion photographed by the endoscope 19 and transmitted through a camera cable and displays it on the display device 11. The CCU 12 outputs the photographic image photographed by the endoscope 19 to the recorder 16 or the printer 17 as necessary. Note that the CCU 12 and the endoscope 19 may be connected to each other via wireless communication.

In addition, the CCU 12 performs an autofocus processing as a processing for performing autofocus (AF) of the endoscope 19. That is, in the endoscope system 1, focus adjustment of the endoscope 19 is automatically performed under control of the CCU 12 regardless of an operator's manipulation.

The light source device 13 is connected to the endoscope 19 through a light guide cable. The light source device 13 outputs light beams having various wavelengths to the endoscope 19 by switching them.

The treatment tool device 14 as a high-frequency output device is connected to the energy treatment tool 20 and the foot switch 26 through a cable. The treatment tool device 14 outputs a high-frequency current to the energy treatment tool 20 in response to a manipulation signal supplied from the foot switch 26.

The pneumoperitoneum device 15 has an air blower unit and an air suction unit. The pneumoperitoneum device 15 blows the air from a hole of the trocar 24 as an opening tool installed in an abdominal wall of an abdomen 31 to the inside of the abdomen 31.

The recorder 16 records a photographic image supplied from the CCU 12.

The printer 17 prints the photographic image supplied from the CCU.

The endoscope 19 is inserted into the abdomen 31 from the hole of the trocar 22 installed in the abdominal wall of the abdomen 31. The endoscope 19 irradiates the inside of the abdomen 31 with the light emitted from the light source device 13 to photograph the inside of the abdomen 31. The endoscope 19 outputs the photographic image obtained by photographing the inside of the abdomen 31 to the CCU 12.

The energy treatment tool 20 includes an electrocautery or the like. The energy treatment tool 20 is inserted into the abdomen 31 from the hole portion of the trocar 23 installed in the abdominal wall of the abdomen 31. The energy treatment tool 20 modifies or removes an inner part of the abdomen 31 using electric heat.

The forceps 21 is inserted into the abdomen 31 from the hole portion of the trocar 25 installed in the abdominal wall of the abdomen 31. The forceps 21 is used to grip an inner part of the abdomen 31. The endoscope 19, the energy treatment tool 20, and the forceps 21 are gripped by an operator, assistant, scopist, robot, or the like.

The foot switch 26 receives a foot manipulation from an operator, assistant, or the like. The foot switch 26 outputs a manipulation signal indicating the received manipulation to the CCU 12 or the treatment tool device 14.

The operator may excise a lesion inside the abdomen 31 while looking at the photographic image displayed on the display device 11 by using the endoscope system 1.

Figure 2:
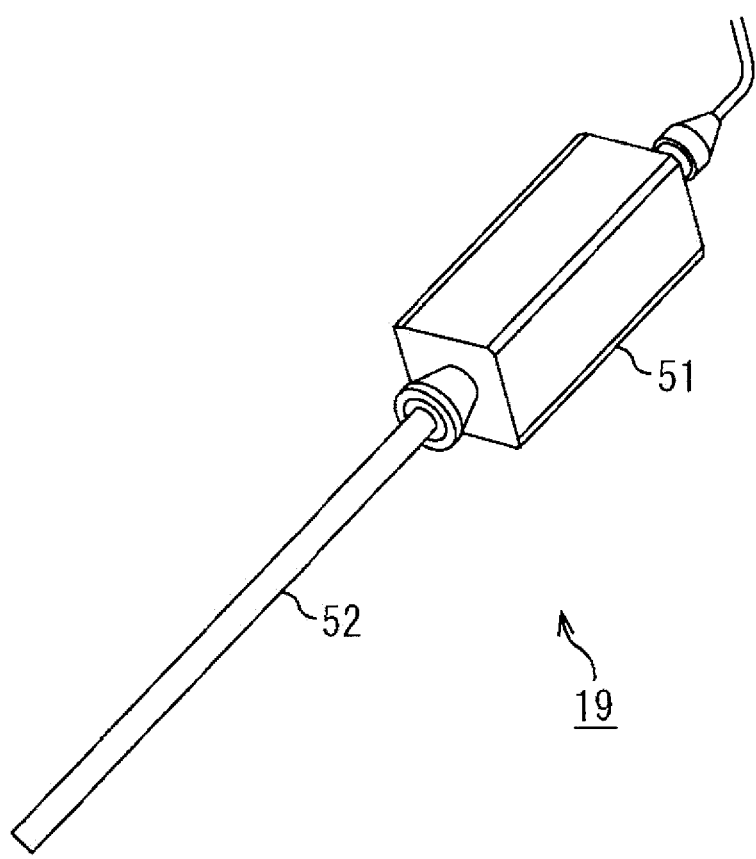
FIG. 2 is a perspective view illustrating appearance of an endoscope.

FIG. 2 is a perspective view illustrating appearance of the endoscope 19.

As illustrated in FIG. 2, the endoscope 19 as a rigid endoscope includes a camera head 51 and a scope 52 having a long lens tube. The endoscopes are classified into a flexible endoscope whose body insertion part is bendable and a rigid endoscope whose body insertion part is unbendable. The endoscope 19 is the latter endoscope. The operator performs a surgical operation by gripping the camera head 51 and inserting the scope 52 into the patient's body.

The camera head 51 internally has an imaging element that performs photoelectric conversion of the light guided by the lens of the scope 52 from the living body, a driving unit for driving the lens of the scope 52, and the like. The camera head 51 irradiates the inside of the abdomen 31 by guiding the light emitted from the light source device 13 via the scope 52 to photograph the surgical treatment portion. The camera head 51 outputs the photographic image obtained from the photographing to the CCU 12 through the camera cable.

The scope 52 is detachably installed in the camera head 51. The scope 52 refers to a plurality of types of scopes having different specifications such as scopes having different diameters (scope diameters) or scopes having different F-numbers of lenses. Which type of scope 52 is employed is appropriately selected depending on details of the surgical operation, a condition of the surgical treatment portion, and the like, and the selected scope 52 is installed in the camera head 51.

Figure 3:
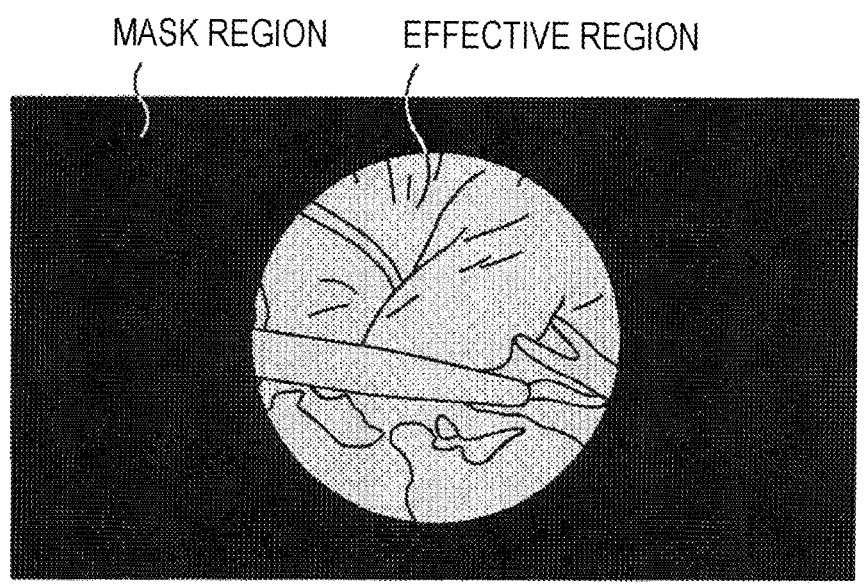
FIG. 3 is a diagram illustrating an exemplary photographic image.

FIG. 3 is a diagram illustrating an exemplary photographic image.

As illustrated in FIG. 3, a circular effective region is formed approximately in the center of an oblong rectangular photographic image, and a dark mask region is formed outward of the effective region.

The mask region is a region formed by an optical shadow (vignetting) of the scope 52. More specifically, vignetting or mechanical vignetting is caused by a difference in an image sensor such as the imaging element 111 which generates medical image data and the scope 52. Since the scope 52 has a long cylindrical shape, a dark region is imaged around the image circle. The condition of the surgical treatment portion is displayed within a range of the effective region having no vignetting. Note that vignetting caused by the scope 52 refers to an optical shadow, for example, generated as an optical path is physically blocked by a side wall of the scope 52.

As described above, the scope 52 is switchable depending on details of the surgical operation or the like. A position of the effective region, a size of the effective region, a shape of the effective region, and the like on the photographic image are changed depending on the type of the scope 52 installed in the camera head 51.

Figure 4A:
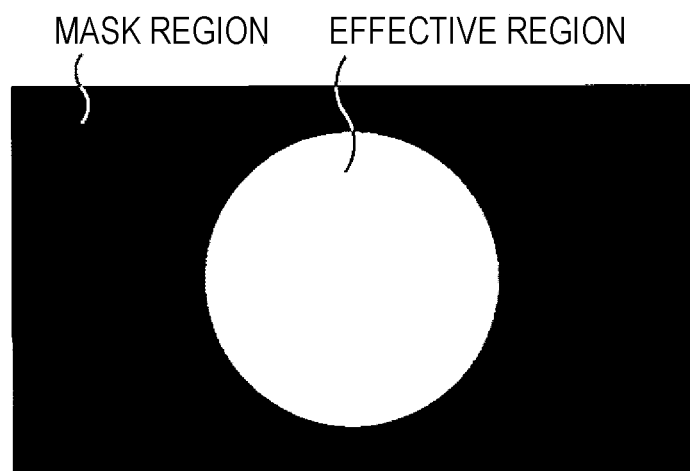
FIG. 4 is a diagram illustrating exemplary photographic images.
Figure 4B:
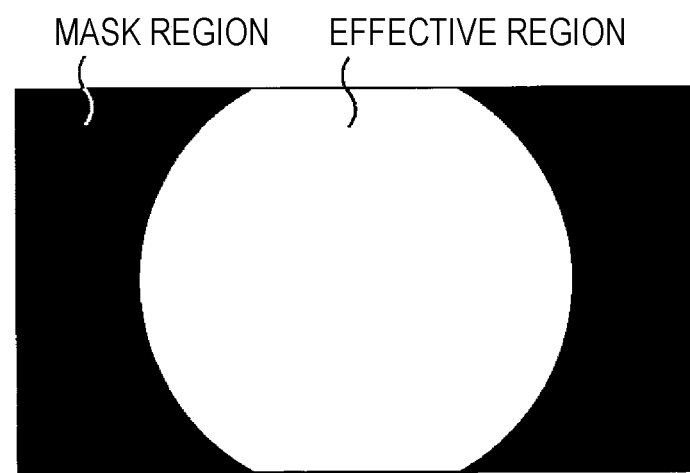

FIGS. 4A and 4B are diagrams illustrating exemplary photographic images. In FIGS. 4A and 4B, the condition of the surgical treatment portion inside the effective region is omitted intentionally for simplicity purposes. Effective image portion data is image data that is obtained from, around, or near the effective region. Mechanical vignetting portion data is image data that is obtained from, around, or near the mask region which is a region formed by an optical shadow (vignetting) of the scope 52.

The photographic image of FIG. 4A is a photographic image obtained in a case where the scope 52 having a scope diameter (diameter) shorter than a vertical length of the photographic image is installed. Similar to the photographic image of FIG. 3, the photographic image of FIG. 4A includes the circular effective region as a whole.

Meanwhile, the photographic image of FIG. 4B is a photographic image obtained in a case where the scope 52 having a scope diameter longer than the vertical length of the photographic image is installed. The effective region of FIG. 4B has a circular shape truncated in the upper end lower ends.

In this manner, an effective region having a diameter corresponding to the scope diameter is formed on the photographic image. A size of the diameter of the scope 52 installed in the camera head 51 can be specified on the basis of the size of the diameter of the effective region included in the photographic image.

As described above, focus adjustment of the endoscope 19 of the endoscope system 1 is automatically performed using the AF.

Assuming that the AF evaluation value as an evaluation value for performing the AF is calculated for the entire photographic image, the AF evaluation values of each region including the mask region are calculated. This is not desirable. Therefore, in a case where the AF evaluation values are calculated for each region including the mask region, for example, an operation for focusing on the edge (border) of the mask region is performed. Evaluation information is one or more evaluation values or other types of information. Evaluation information includes at least information which comes from effective image portion data.

In addition, assuming that the calculation target region for the AF evaluation value is fixedly set inside the effective region, the target region is restricted to a narrow range of the vicinity of the center of the photographic image corresponding to the effective region regardless of which scope 52 is installed. As illustrated in FIGS. 4A and 4B, the range of the effective region changes depending on the type of the installed scope 52.

In the CCU 12, the diameter of the scope 52 installed in the endoscope 19, the center position of the effective region, and the like are specified on the basis of the photographic image, and the evaluation value calculation target region as a region for calculating the AF evaluation value is set inside the effective region on the basis of the specified information. In addition, the AF evaluation value is calculated for the evaluation value calculation target region to perform the autofocus processing.

Since the AF evaluation value is calculated for the evaluation value calculation target region set within the effective region to perform the autofocus processing, the CCU 12 can reliably focus on the surgical treatment portion imaged on the effective region.

A series of processes of the CCU 12 for performing the autofocus processing by setting the evaluation value calculation target region depending on the scope 52 installed in the endoscope 19 in this manner will be described below.

First Embodiment: Example of Detecting Mask Region on the Basis of Sampling Value <Exemplary Configurations of CCU and Endoscope>

Figure 5:
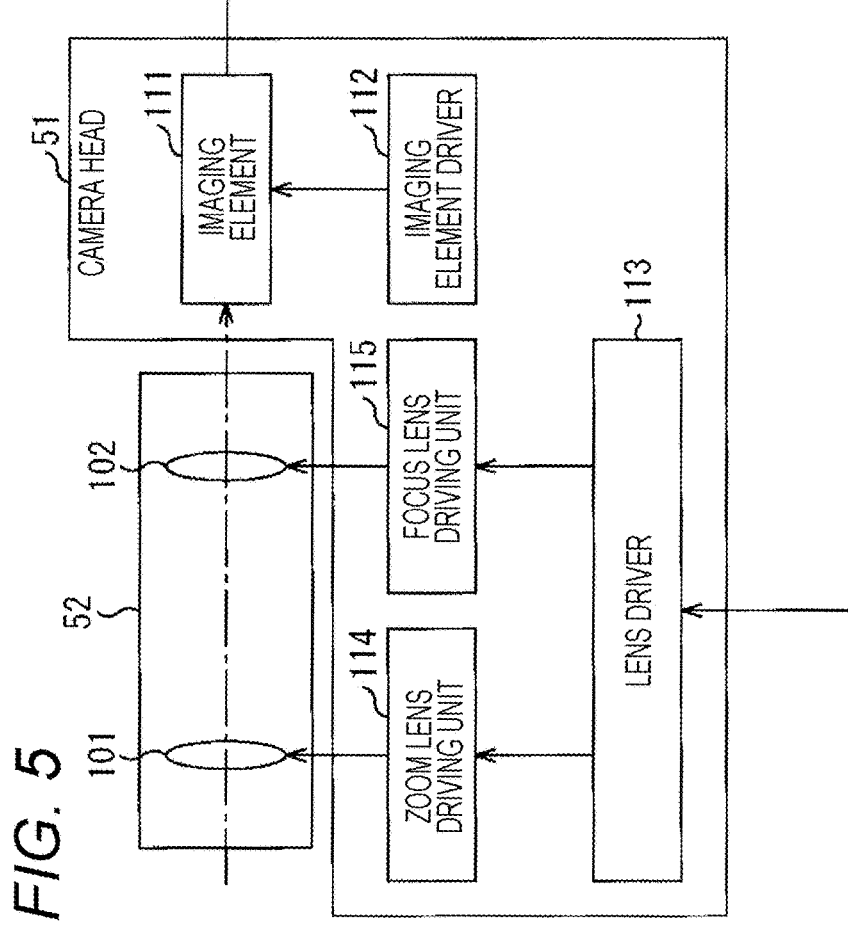
FIG. 5 is a block diagram illustrating exemplary configurations of a CCU and an endoscope.

FIG. 5 is a block diagram illustrating exemplary configurations of the CCU 12 and the endoscope 19.

As illustrated in the left half of FIG. 5, the camera head 51 includes an imaging element 111, an imaging element driver 112, a lens driver 113, a zoom lens driving unit 114, and a focus lens driving unit 115.

The imaging element 111 includes, for example, a CMOS image sensor or a CCD image sensor. The imaging element 111 converts an optical image focused on an imaging surface into an electric signal by photoelectric conversion and outputs the electric signal as a photographic signal to the CCU 12.

The imaging element driver 112 is a driver for driving the imaging element 111. The imaging element driver 112 allows the imaging element 111 to perform a predetermined operation such as a photographing operation or a reset operation by outputting a drive signal. For example, a shutter speed of the imaging element 111 is controlled, for example, by the drive signal output from the imaging element driver 112.

The lens driver 113 includes a processor such as a central processing unit (CPU) or a digital signal processor (DSP). The lens driver 113 controls the operations of the zoom lens driving unit 114 and the focus lens driving unit 115 depending on a control signal supplied from the CCU 12.

The zoom lens driving unit 114 adjusts a photographic magnification ratio by moving the zoom lens 101 of the scope 52 along an optical axis.

The focus lens driving unit 115 performs focus adjustment by moving the focus lens 102 of the scope 52 along an optical axis.

As illustrated in the right half of FIG. 5, the CCU 12 includes a camera signal processing unit 131, a sampling frame gate 132, a sampling unit 133, a mask detection unit 134, an AF sampling unit 135, and a lens controller 136.

The camera signal processing unit 131 applies various types of signal processings such as a white balance processing and a γ correction processing to the photographic signal supplied from the imaging element 111.

The camera signal processing unit 131 outputs the photographic signal obtained through the signal processing to the display device 11 as a video signal. The image of the surgical treatment portion is displayed on the display device 11 on the basis of the video signal output from the camera signal processing unit 131. The photographic signal output from the camera signal processing unit 131 is also supplied to the sampling frame gate 132.

The sampling frame gate 132 sets a sampling frame in a predetermined region on the photographic image under control of the lens controller 136. For example, the sampling frame is set in a predetermined region of the photographic image including the mask region before detection of the mask region. In addition, the sampling frame is set in the effective region after detection of the mask region.

The sampling frame gate 132 outputs a photographic signal of the pixels of the sampling frames out of the photographic signals supplied from the camera signal processing unit 131. The photographic signal output from the sampling frame gate 132 is supplied to the sampling unit 133 and the AF sampling unit 135.

The sampling unit 133 performs sampling for the photographic signal supplied from the sampling frame gate 132 and outputs sampling values of each sampling frame to the mask detection unit 134. For example, the sampling unit 133 integrates luminance values of pixels of each sampling frame to obtain a result of the integration as the sampling value.

The mask detection unit 134 detects an edge of the mask region on the basis of the sampling value supplied from the sampling unit 133. Although the mask detection unit 134 detects the edge of the mask region in this description, the edge detection of the mask region also includes edge detection of the effective region.

The mask detection unit 134 specifies a diameter of the scope 52 installed in the camera head 51 on the basis of a position of the detected edge of the mask region. In addition, the mask detection unit 134 specifies a center position of the effective region and a position (range) of the mask region on the basis of the edge position of the mask region.

The mask detection unit 134 outputs information regarding the scope diameter, the center position of the effective region, and the position of the mask region to the lens controller 136 as a result of the mask detection. As described below, detection of the mask region using the mask detection unit 134 may also be performed on the basis of the AF evaluation value obtained by the AF sampling unit 135 in some cases.

The AF sampling unit 135 calculates the AF evaluation value on the basis of the photographic signal supplied from the sampling frame gate 132. For example, the AF sampling unit 135 calculates the AF evaluation value representing contrast by calculating a second-order derivative for the luminance signals of all pixels of the AF sampling frames. Note that, in general, a difference of the luminance signal between neighboring pixels increases, and the contrast increases in a focused state, compared to an unfocused state.

The AF evaluation value calculated by the AF sampling unit 135 is supplied to the lens controller 136 and is also supplied to the mask detection unit 134 appropriately.

The lens controller 136 adjusts a position of the zoom lens 101 by outputting the control signal to the lens driver 113 of the camera head 51.

The lens controller 136 also outputs the control signal to the lens driver 113 of the camera head 51 and adjusts a position of the focus lens 102. A process of adjusting the position of the focus lens 102 by outputting the control signal corresponds to the autofocus processing for performing the AF of the endoscope 19. The control signal in this case is a signal containing at least a position of the focus lens 102 of the lens driver 113 or a displacement of a position of the focus lens 102 as an AF control parameter.

The lens controller 136 adjusts a shutter speed or an ISO sensitivity of the imaging element 111 by appropriately outputting a control signal to the imaging element driver 112 of the camera head 51. A process of adjusting the shutter speed or the ISO sensitivity by outputting the control signal and controlling exposure regardless of an operator's manipulation corresponds to the automatic exposure processing for performing the AE. As described below, the AE function is implemented on the basis of the detection result of the mask region. The control signal in this case is a signal containing at least the speed value of the shutter speed or the sensitivity value of the ISO sensitivity as an AE control parameter.

A focus command signal, a zoom command signal, a manual/automatic focus conversion signal, and the like are input to the lens controller 136 in response to an operator's manipulation. The zoom command signal is a signal representing details of the zoom adjustment performed by the operator, and the focus command signal is a signal representing details of the focus adjustment performed by the operator.

The manual/automatic focus conversion signal is a conversion signal for indicating whether the focus adjustment is performed in a manual mode or in an autofocus mode. The focus command signal is input in a case where an option for performing the focus adjustment in the manual mode is selected. The CCU 12 and/or the camera head 51 are illustrated and described as including various units, processors, CPUs, controllers, drivers, etc. These elements and other elements of the invention can be implemented using circuitry configured to perform the functionality disclosed herein. Moreover, in some embodiments, electronic circuitry or processing circuitry including, for example, a microprocessor, programmable logic circuitry, field-programmable gate arrays (FPGA), or programmable logic arrays (PLA) may execute computer readable program instructions by using information from the computer readable program instructions to configure or customize the electronic circuitry, in order to perform aspects of the present disclosure.

<Detection of Mask Region>

Figure 6:
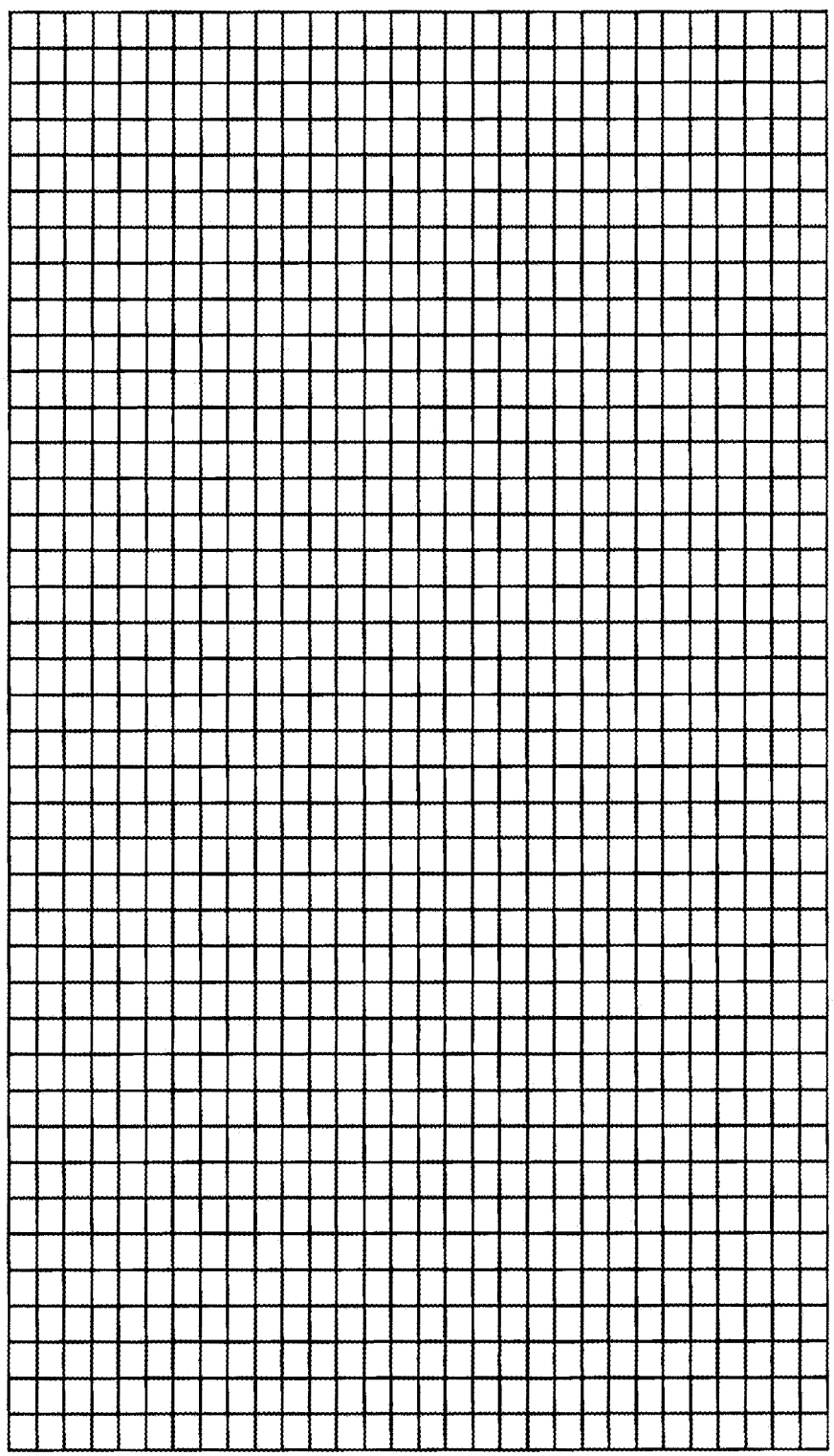
FIG. 6 is a diagram illustrating an exemplary setting of sampling frames.

FIG. 6 is a diagram illustrating an exemplary setting of the sampling frame.

The sampling frames are set, for example, across the entire area of the photographic image. In the example of FIG. 6, thirty sampling frames set in a column (vertical) direction and forty sampling frames set in a row (horizontal) direction are arranged in a matrix shape across the entire area of the photographic image. A total size of the sampling frames in FIG. 6 is equal to the size of the photographic image.

The mask detection unit 134 detects an edge of the mask region on the basis of the a thousand and two hundred (1200) sampling values obtained from the photographic signal of the pixels of each sampling frame.

In this manner, the sampling frames are set for the photographic image such that a resolution sufficient to detect an edge of the mask region can be provided.

Note that, although the total size of the sampling frames is equally set to the size of photographic image in the example of FIG. 6, the size of the sampling frames may be set to a range smaller than the size of the photographic image. In addition, the number of the sampling frames may also be set arbitrarily.

Figure 7:
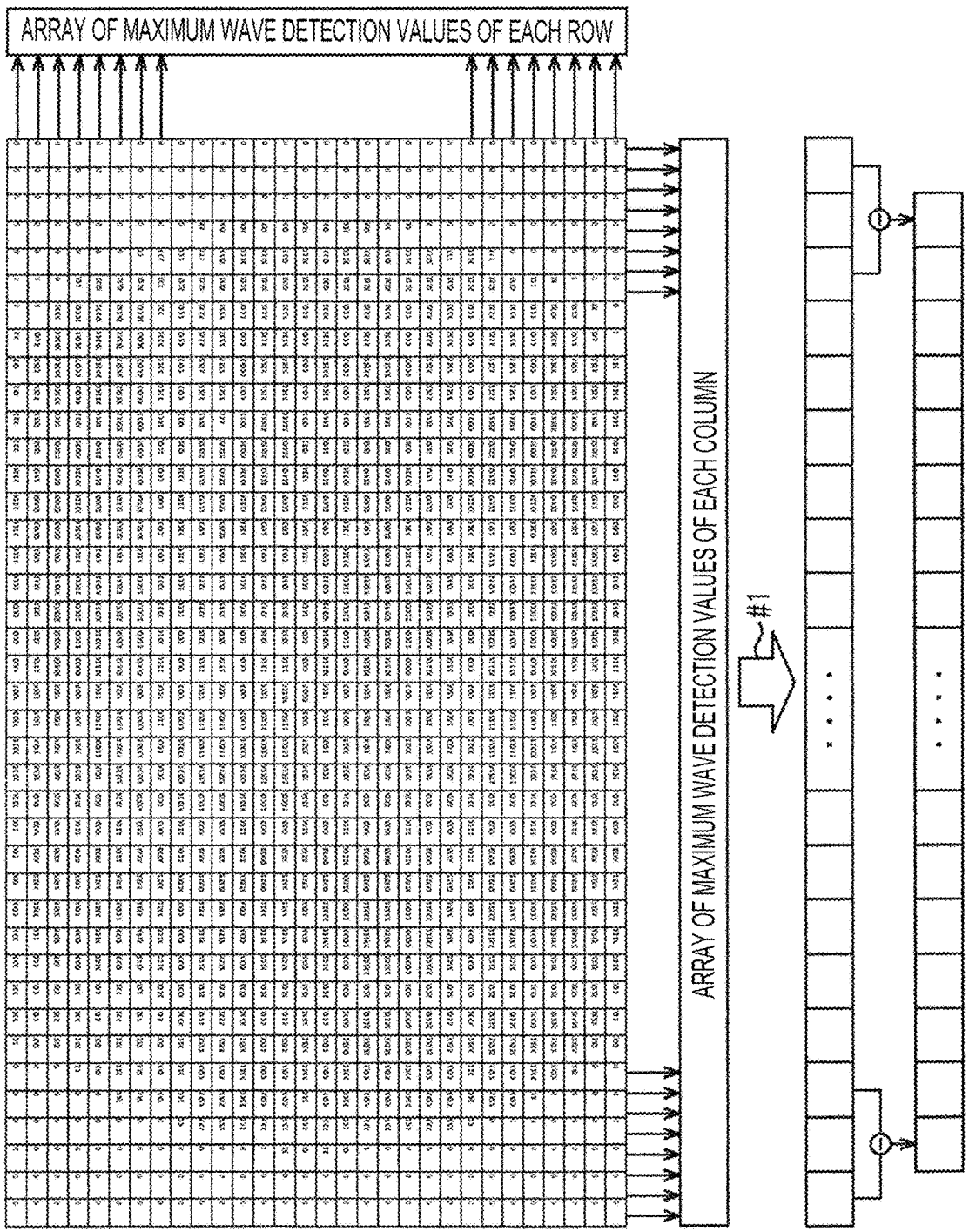
FIG. 7 is a diagram illustrating exemplary edge detection of a mask region.

FIG. 7 is a diagram illustrating an example of the edge detection in the mask region.

A series of letters "x" inserted into each sampling frame respectively refer to predetermined sampling values. Sampling frames having a numerical value "0" refer to sampling frames having a sampling value of zero, which means a sampling frame including a black pixel.

In a case where the sampling values are obtained by the sampling unit 133 in this manner, the mask detection unit 134 of FIG. 5 obtains a maximum sampling value out of the sampling values of the sampling frames of each column and a maximum sampling value out of the sampling values of the sampling frames of each row.

In addition, the mask detection unit 134 obtains differences between sampling values of every other column in a sequence of maximum sampling values of each column as illustrated before a void arrow #1. Similarly, for the row direction, the mask detection unit 134 obtains differences between sampling values of every other row in a sequence of maximum sampling values of each row.

For example, the mask detection unit 134 sequentially calls the differences between the sampling values of every other column starting from the leftmost difference and detects a position of the column where a difference equal to or larger than a threshold value is obtained as a left edge position of the mask region. In addition, the mask detection unit 134 sequentially calls the differences between the sampling values of every other column starting from the rightmost difference and detects a position of the column where a difference equal to or larger than a threshold value is obtained as a right edge position of the mask region.

Similarly, for the row direction, the mask detection unit 134 sequentially calls the differences between the sampling values of every other row starting from the uppermost difference and detects a position of the row where a difference equal to or larger than threshold value is obtained as an upper edge position of the mask region. In addition, the mask detection unit 134 sequentially calls the differences between the sampling values of every other row starting from the lowermost difference and detects a position of the row where a difference equal to or larger than a threshold value is obtained as a lower edge position of the mask region.

Figure 8:
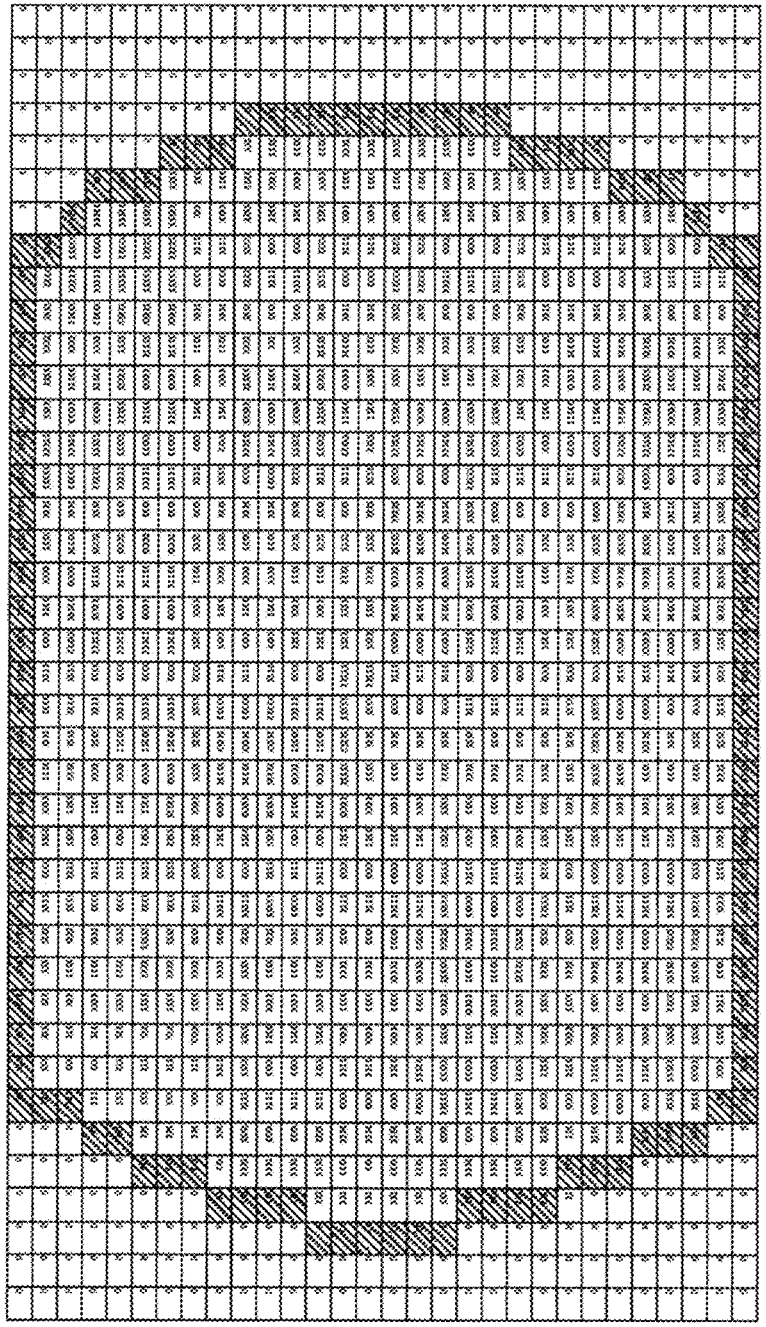
FIG. 8 is a diagram illustrating exemplary edge detection of a mask region.

On the basis of the upper, lower, left, and right edge positions and a fact that the effective region has a circular shape, the mask detection unit 134 detects all edges surrounding the effective region as illustrated in FIG. 8.

In FIG. 8, the hatched sampling frames are sampling frames of the positions detected as edges of the mask region. The sampling frames positioned outward of the hatched sampling frames belong to the mask region, and the inward sampling frames (including the hatched sampling frames) belong to the effective region.

Note that, in a case where the effective region has a large diameter, and the upper and lower ends of the effective region are truncated, the left and right edges are detected on the basis of the differences of the sampling values of every other column to specify the mask region. In addition, in a case where no edge is detected, it is specified that there is no mask region.

In a case where the mask region and the effective region are detected, the mask detection unit 134 specifies, for example, an average edge width as a diameter of the effective region, that is, as a scope diameter on the basis of the edge width of the effective region. In addition, the mask detection unit 134 specifies a position indicated by an average median value of the edge width as a center position of the effective region. Note that a table where a range of the average edge width and corresponding scope diameters are associated with each other may be stored in advance, and the scope diameter may be specified by referencing the table on the basis of the obtained average edge width.

Information indicating the scope diameter and the center position of the effective region is supplied to the lens controller 136 along with information regarding the position of the mask region. The lens controller 136 performs a setting of sampling frames used in calculation of the AF evaluation value and the like on the basis of the detection result of the mask region.

Second Embodiment: Example of Detecting Mask Region on the Basis of AF Evaluation Value The mask region may be detected on the basis of the AF evaluation value obtained by the AF sampling unit 135 instead of the sampling value obtained by the sampling unit 133.

First Exemplary Setting

Figure 9:
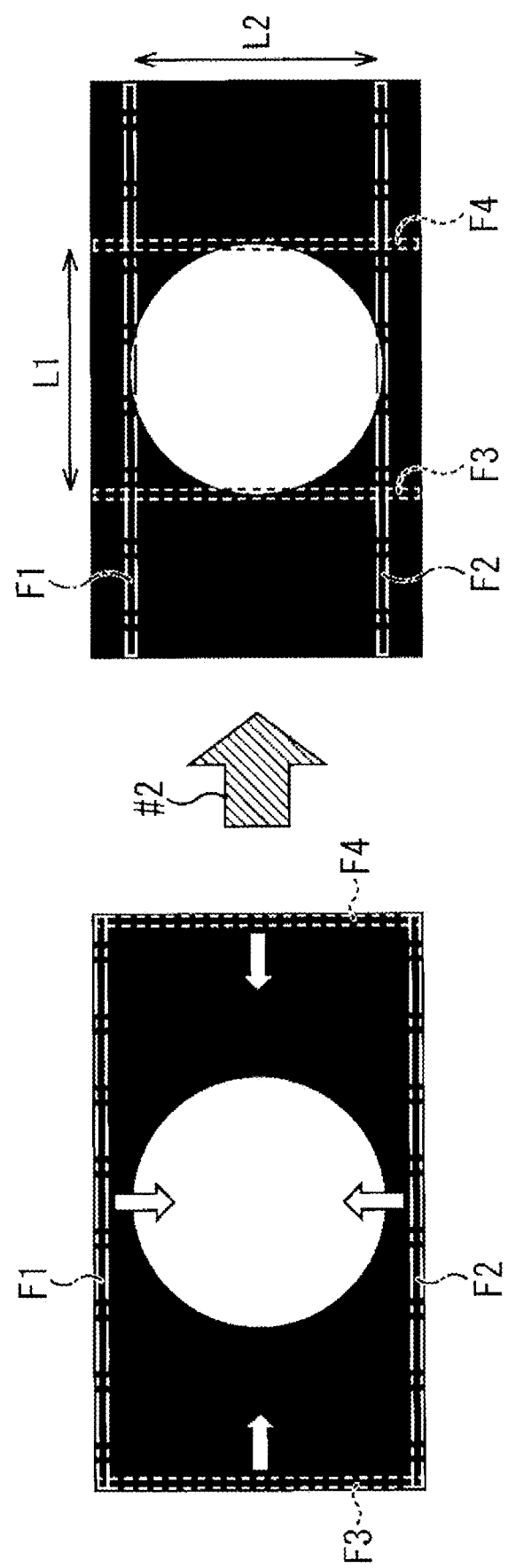
FIG. 9 is a diagram illustrating an exemplary setting of sampling frames in a case where the mask region is detected on the basis of the AF evaluation value.

FIG. 9 is a diagram illustrating an exemplary setting of the sampling frames in a case where the mask region is detected on the basis of the AF evaluation value.

As indicated by the sampling frames F1 to F4 of the left photographic image of FIG. 9, the sampling frame gate 132 sets sampling frames, for example, having a narrow strip shape in the upper, lower, left, and right ends of the photographic image. The sampling frames F1 to F4 are set, for example, under control of the lens controller 136.

The sampling frames F1 and F2 indicated by one-dotted chain lines are sampling frames for detecting upper and lower edges, respectively, of the mask region. In addition, the sampling frames F3 and F4 indicated by dotted lines are sampling frames for detecting left and right edges, respectively, of the mask region.

In addition, as indicated by the void arrows, the sampling frame gate 132 moves positions of the sampling frames F1 to F4 toward a center of the photographic image.

The AF sampling unit 135 sequentially calculates the AF evaluation values on the basis of the photographic signals corresponding to the pixels within the sampling frames set by changing the positions in this manner.

In a case where a change equal to or larger than a threshold value is generated in the AF evaluation value calculated by the AF sampling unit 135, the mask detection unit 134 specifies the position where the change is detected as an edge position of the mask region. For example, as indicated before the arrow #2, when each of the sampling frames F1 to F4 is set as the edge position of the mask region, a change of the AF evaluation value equal to or larger than the threshold value is detected.

The mask detection unit 134 specifies a diameter of the scope installed in the camera head 51, a center position of the effective region, and a position of the mask region on the basis of a distance L1 between the sampling frames F1 and F2 and a distance L2 between the sampling frames F3 and F4. For example, an average value of the distances L1 and L2 is specified as the scope diameter, and a position indicated by an average median value of the edge is specified as a center position of the effective region.

Second Exemplary Setting

Figure 10:
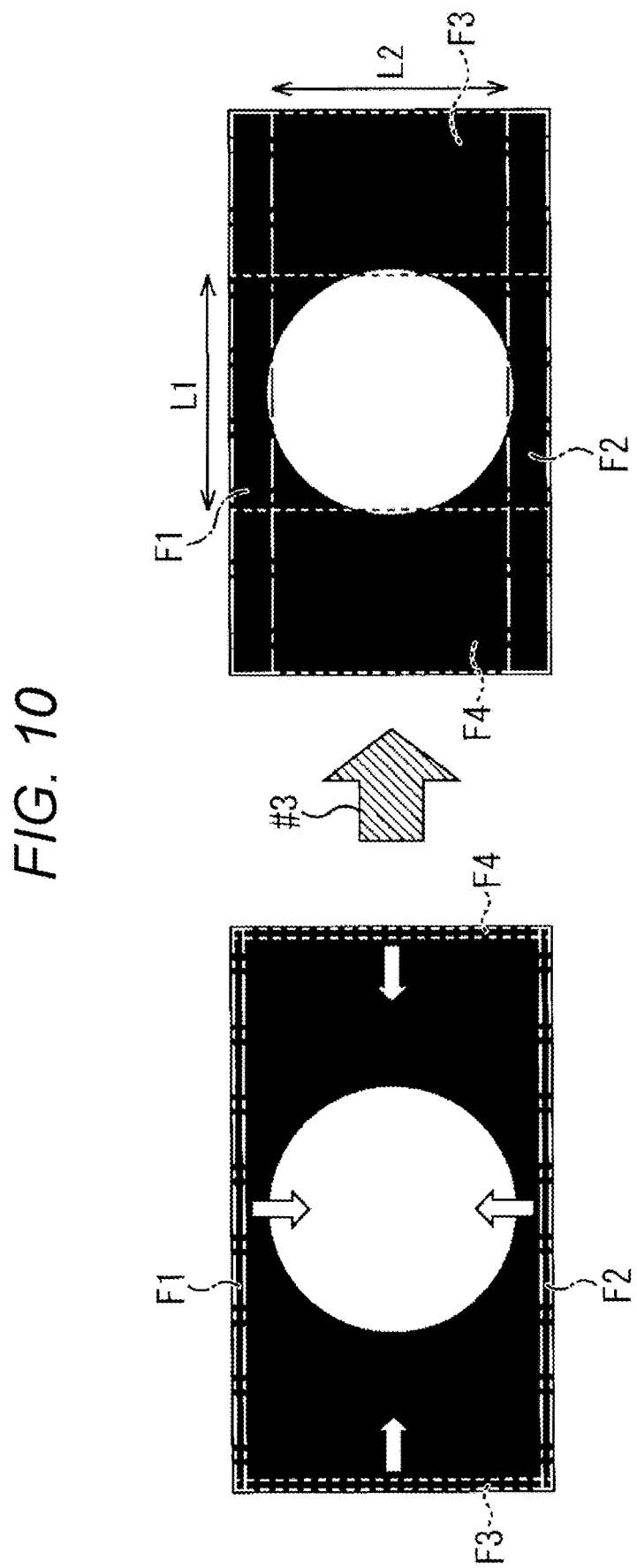
FIG. 10 is a diagram illustrating another exemplary setting of sampling frames in a case where a mask region is detected on the basis of the AF evaluation value.

FIG. 10 is a diagram illustrating another exemplary setting of the sampling frame in a case where the mask region is detected on the basis of the AF evaluation value.

The method of setting the sampling frame of FIG. 10 is different from the method of setting the sampling frame of FIG. 9 in that the sampling frames F1 to F4 are set such that the width is sequentially widened instead of changing the positions of the sampling frames F1 to F4. The widths of the sampling frames F1 to F4 are sequentially widened by moving inner edges of the narrow strip-like sampling frames F1 to F4 set in the upper, lower, left, and right ends of the photographic image toward a center of the photographic image as indicated by the void arrows.

The AF sampling unit 135 sequentially calculates the AF evaluation value on the basis of the photographic signals corresponding to the pixels of the sampling frames set by changing the width.

In a case where a change equal to or larger than a threshold value occurs in the AF evaluation value calculated by the AF sampling unit 135, the mask detection unit 134 specifies an inner edge position of the sampling frame where the change is detected as the edge position of the mask region. For example, as indicated before the arrow #3, a change of the AF evaluation value equal to or larger than the threshold value is detected when the inner edges of the sampling frames F1 to F4 are set as the respective edge positions of the mask region.

The mask detection unit 134 specifies the diameter of the scope installed in the camera head 51, the center position of the effective region, and the position of the mask region on the basis of the distance L1 between the sampling frames F1 and F2 and the distance L2 between the sampling frames F3 and F4.

Third Exemplary Setting

FIG. 11 is a diagram illustrating further another exemplary setting of the sampling frame in a case where the mask region is detected on the basis of the AF evaluation value.

The method of setting the sampling frame of FIG. 11 is different from the setting methods of FIG. 9 and the like in that a plurality of small sampling frames having an approximately square shape in an initial state are set instead of the narrow strip-like sampling frames.

That is, as illustrated in the left half of FIG. 11, the sampling frame gate 132 sets sampling frames F1-1 to F1-3 having an approximately square shape in the upper end of the photographic image and sets sampling frames F2-1 to F2-3 having an approximately square shape in the lower end of the photographic image. The sampling frame gate 132 sets sampling frames F3-1 to F3-3 having an approximately square shape in the left end of the photographic image and sets sampling frames F4-1 to F4-3 having an approximately square shape in the right end of the photographic image.

Furthermore, the sampling frame gate 132 moves positions of each sampling frame toward the center of the photographic image or widens the width of the sampling frame toward the center of the photographic image.

The AF sampling unit 135 sequentially calculates the AF evaluation values on the basis of the photographic signals corresponding to the pixels of the sampling frames set by changing the position or the width.

In a case where a change equal to or larger than a threshold value occurs in the AF evaluation value calculated by the AF sampling unit 135, the mask detection unit 134 specifies the position where the change is detected as the edge position of the mask region.

For example, as illustrated before the arrow #4, a change of the AF evaluation value equal to or larger than the threshold value is detected when the sampling frames F1-1 to F1-3 and F2-1 to F2-3 having an approximately square shape are set as the respective edge positions of the mask region.

In addition, a change of the AF evaluation value equal to or larger than the threshold value is detected when the inner edges of the sampling frames F3-1 to F3-3 and F4-1 to F4-3 reach the respective edge positions of the mask region.

The mask detection unit 134 specifies the diameter of the scope installed in the camera head 51, the center position of the effective region, and the position of the mask region on the basis of the distance between the opposite sampling frames.

Although, in the example of FIG. 11, the sampling frames F1-1 to F1-3 and F2-1 to F2-3 set in the upper and lower ends of the photographic image are set by changing the positions rather than the shapes, they may also be set by changing the widths. Furthermore, although the sampling frames F3-1 to F3-3 and F4-1 to F4-3 set in the left and right ends, respectively, of the photographic image are set by changing the widths, they may also be set by changing the positions rather than the shapes.

The method of setting the sampling frames by changing the shapes and the method of setting the sampling frames by changing the widths may also be used in combination. It is possible to detect a specific shape of the edge of the mask region by changing the position or width of the small sampling frame.

Note that, in a case where the diameter of the effective region is large, and the effective region is vertically disconnected, the mask region is detected only on the basis of the AF evaluation values calculated from the sampling frames set in the left and right sides. In addition, in a case where no edge is found, it is determined that there is no mask region.

Information indicating the scope diameter specified from the AF evaluation value and the center position of the effective region is supplied to the lens controller 136 along with the information regarding the position of the mask region. The lens controller 136 sets the sampling frame used in calculation of the AF evaluation value or performs other controls on the basis of the detection result of the mask region.

Third Embodiment: First Exemplary Setting of Evaluation Value Calculation Target Region FIGS. 12A and 12B are diagrams illustrating an exemplary setting of the evaluation value calculation target region.

Figure 12A:
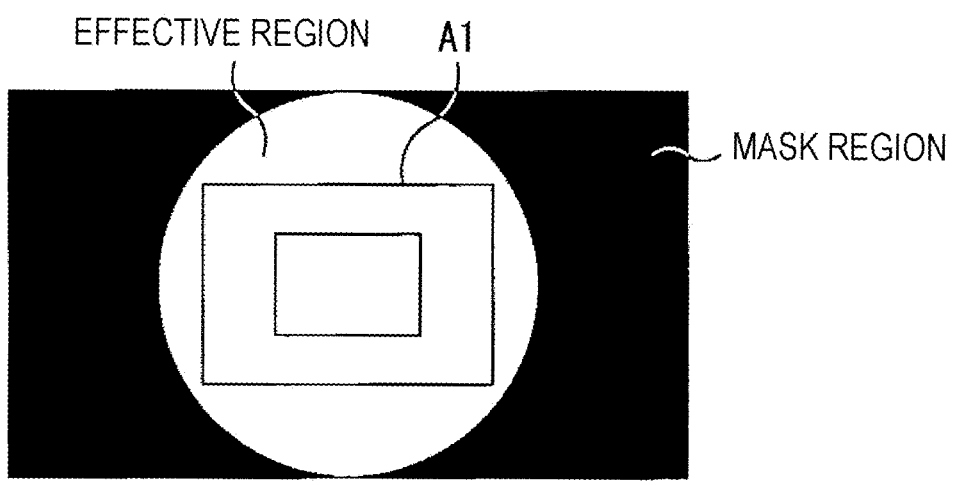
FIG. 12 is a diagram illustrating an exemplary setting of an evaluation value calculation target region.
Figure 12B:
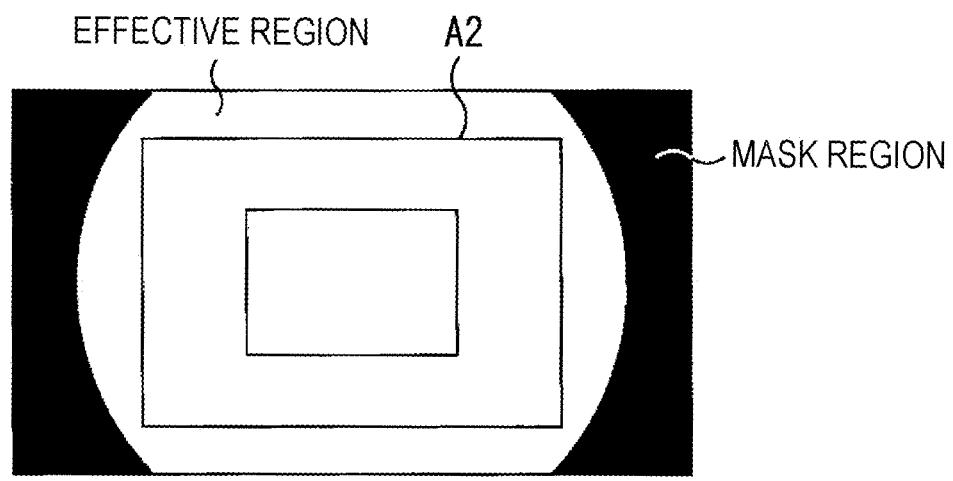

As illustrated in FIGS. 12A and 12B, the lens controller 136 sets the evaluation value calculation target region serving as a target region for calculating the AF evaluation value inside the effective region so as not to overlap with the mask region. For example, the evaluation value calculation target region is set by magnifying or reducing a size of a default area and shifting a default center position on the basis of the detection result of the mask region.

The oblong area A1 of FIG. 12A is an evaluation value calculation target region set inside the effective region having a diameter shorter than the vertical length of the photographic image. The area A2 of FIG. 12B is an evaluation value calculation target region set inside the effective region having a diameter longer than the vertical length of the photographic image.

Any evaluation value calculation target region is set such that the entire area is included in the effective region. In FIGS. 12A and 12B, two oblong rectangles representing the evaluation value calculation target regions are inserted into the effective region in order to show that any size can be set for the evaluation value calculation target region as long as it is included in the effective region.

Note that, although the evaluation value calculation target region has an oblong rectangular shape in the example of FIGS. 12A and 12B, other shapes such as a square shape and a circular shape may also be employed.

Information regarding such an evaluation value calculation target region is supplied from the lens controller 136 to the sampling frame gate 132, so that the sampling frame serving as a calculation target of the AF evaluation value is set inside the evaluation value calculation target region.

The AF sampling unit 135 calculates the AF evaluation value on the basis of the photographic signal of the pixel of the sampling frame set in the evaluation value calculation target region. In addition, the lens controller 136 also performs the autofocus processing on the basis of the calculated AF evaluation value.

As a result, the CCU 12 can reliably focus on the surgical treatment portion imaged on the effective region.

Fourth Embodiment: Second Exemplary Setting of Evaluation Value Calculation Target Region FIGS. 13A and 13B are diagrams illustrating another exemplary setting of the evaluation value calculation target region.

Figure 13A:
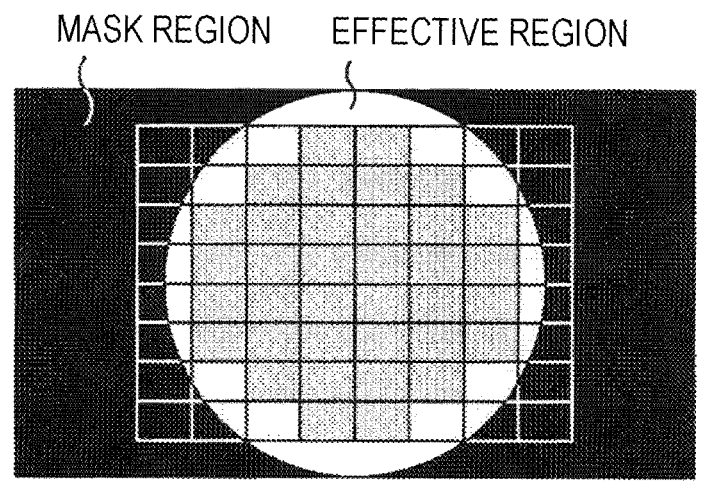
FIG. 13 is a diagram illustrating another exemplary setting of the evaluation value calculation target region.
Figure 13B:
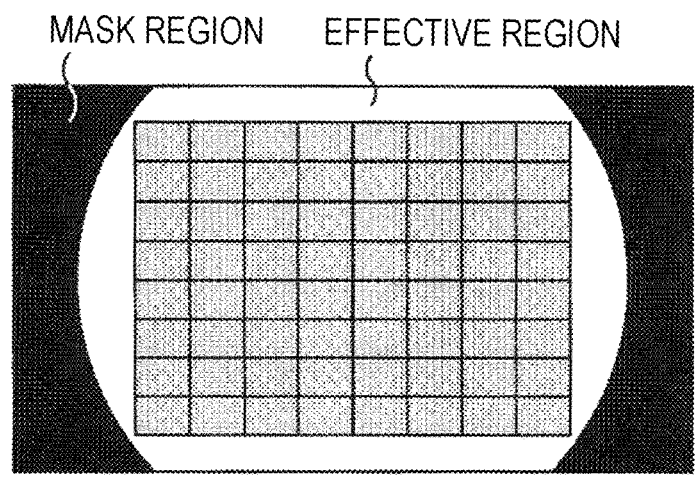

Each segment of the mesh pattern overlapping on the photographic image of FIGS. 13A and 13B represents a sampling frame. In the example of FIGS. 13A and 13B, a plurality of sampling frames (eight sampling frames in the vertical direction and eight frames in the horizontal direction) are set side by side in a matrix shape around the center of the photographic image. In this example, the positions of the sampling frames are fixed regardless of the range of the effective region. The photographic signals of the pixels of each sampling frame are supplied from the sampling frame gate 132 to the AF sampling unit 135.

Out of the sampling frames fixedly set in this manner, the lens controller 136 selects the sampling frames entirely included in the effective region without overlapping with the mask region as the evaluation value calculation target region serving as a calculation target for the AF evaluation value. The sampling frames colored in FIGS. 13A and 13B are sampling frames selected as the evaluation value calculation target region. Meanwhile, the sampling frames overlapping with the mask region are treated as invalid sampling frames (having a weight of zero).

The lens controller 136 outputs information regarding the sampling frame selected as the evaluation value calculation target region to the AF sampling unit 135 to calculate the AF evaluation value for the sampling frame selected as the evaluation value calculation target region.

That is, in the example of FIGS. 12A and 12B, the sampling frames serving as the calculation target of the AF evaluation value are set on the basis of the detection result of the mask region. In comparison, in the example of FIGS. 13A and 13B, the sampling frames serving as the calculation target of the AF evaluation value are selected from the sampling frames set in advance.

In the example of FIG. 13A, out of the sampling frames set in advance, a part of the sampling frames included in the effective region are set as the evaluation value calculation target region. In addition, in the example of FIG. 13B, since all of the sampling frames set in advance are included in the effective region, all of the sampling frames are set as the evaluation value calculation target region.

Note that, although all of the sampling frames included in the effective region are set as the evaluation value calculation target region in the example of FIGS. 13A and 13B, a part of the sampling frames included in the effective region may also be set as the evaluation value calculation target region.

Information regarding such an evaluation value calculation target region is supplied from the lens controller 136 to the AF sampling unit 135, and the AF evaluation value is calculated on the basis of the pixel signals of the pixels of the sampling frames set as the evaluation value calculation target region. In addition, the lens controller 136 performs the autofocus processing on the basis of the calculated AF evaluation value.

As a result, the CCU 12 can reliably focus on the surgical treatment portion imaged on the effective region.

Fifth Embodiment: Exemplary Autofocus Processing

An F-number of the scope 52 may be estimated on the basis of the scope diameter, the center position of the effective region, and the position of the mask region specified as described above, and a depth of focus may be obtained on the basis of the estimated F-number.

The F-number and the depth of focus of the scope 52 are used by the lens controller 136 in order to set parameters for defining details of the autofocus processing, such as an AF speed, focus accuracy, and a wobbling amplitude, for example. The lens controller 136 calculates each of the AF speed, the focus accuracy, and the wobbling amplitude on the basis of the F-number and the depth of focus of the scope 52 and performs the autofocus processing on the basis of the calculation result.

As a result, the lens controller 136 can perform the autofocus processing with higher accuracy. Note that a table regarding a relationship between the F-numbers, the depths of focus of the scope, and the scope diameters may be stored in advance, and the F-numbers and the depths of focus may be obtained by referencing the table.

Operation of CCU

AF Processing

An AF processing of the CCU 12 will be described with reference to the flowchart of FIG. 14.

Figure 14:
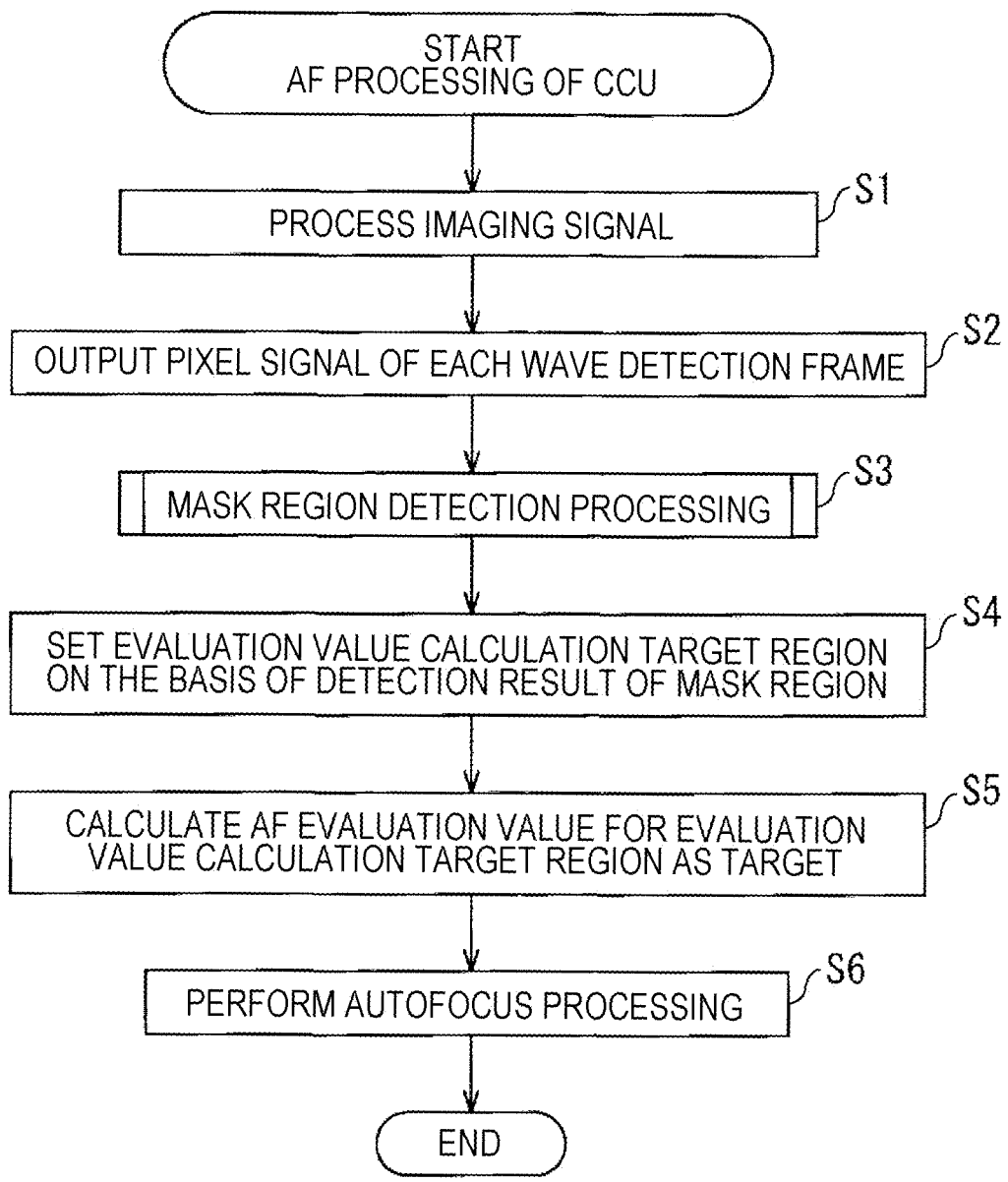
FIG. 14 is a flowchart for describing an AF processing of the CCU.

The process of FIG. 14 starts, for example, when the endoscope 19 photographs a surgical treatment portion, and a photographic signal is supplied from the imaging element 111.

In step S1, the camera signal processing unit 131 applies various types of signal processings such as the white balance processing to the photographic signal supplied from the imaging element 111.

In step S2, the sampling frame gate 132 outputs the photographic signal of the pixel of each sampling frame.

For example, in a case where the mask region is detected as described in conjunction with FIGS. 7 and 8, the photographic signals of the pixels of each sampling frame set for the entire photographic image are output from the sampling frame gate 132 and are supplied to the sampling unit 133.

In addition, in a case where the mask region is detected as described in conjunction with FIGS. 9, 10, and 11, the photographic signals of the pixels of each sampling frame set in predetermined positions of the photographic image are output from the sampling frame gate 132 and are supplied to the AF sampling unit 135.

In step S3, a mask region detection process is performed. Information regarding the scope diameter, the center position of the effective region, and the position of the mask region specified in the mask region detection process is supplied from the mask detection unit 134 to the lens controller 136. Details of the mask region detection process will be described below with reference to the flowcharts of FIGS. 15 and 16.

In step S4, the lens controller 136 sets the evaluation value calculation target region on the basis of the detection result of the mask region.

In a case where the evaluation value calculation target region is set as described in conjunction with FIGS. 12A and 12B, the lens controller 136 outputs information regarding the evaluation value calculation target region to the sampling frame gate 132 and sets the sampling frames in the evaluation value calculation target region.

In addition, in a case where the evaluation value calculation target region is set as described in conjunction with FIGS. 13A and 13B, the lens controller 136 outputs information regarding the evaluation value calculation target region to the AF sampling unit 135 and calculates the AF evaluation value for the sampling frame selected as the evaluation value calculation target region.

In step S5, the AF sampling unit 135 calculates the AF evaluation value for the sampling frame of the evaluation value calculation target region as a target on the basis of the photographic signal supplied from the sampling frame gate 132.

In step S6, the lens controller 136 performs the autofocus processing on the basis of the AF evaluation value calculated by the AF sampling unit 135. A control signal is output from the lens controller 136 to the lens driver 113 of the camera head 51 to adjust the position of the focus lens 102. As a result, the AF is implemented.

The aforementioned processes are repeated while the photographic signal is supplied from the imaging element 111.

<Mask Region Detection Process>

Next, the mask region detection process performed in step S3 of FIG. 14 will be described with reference to the flowchart of FIG. 15.

Figure 15:
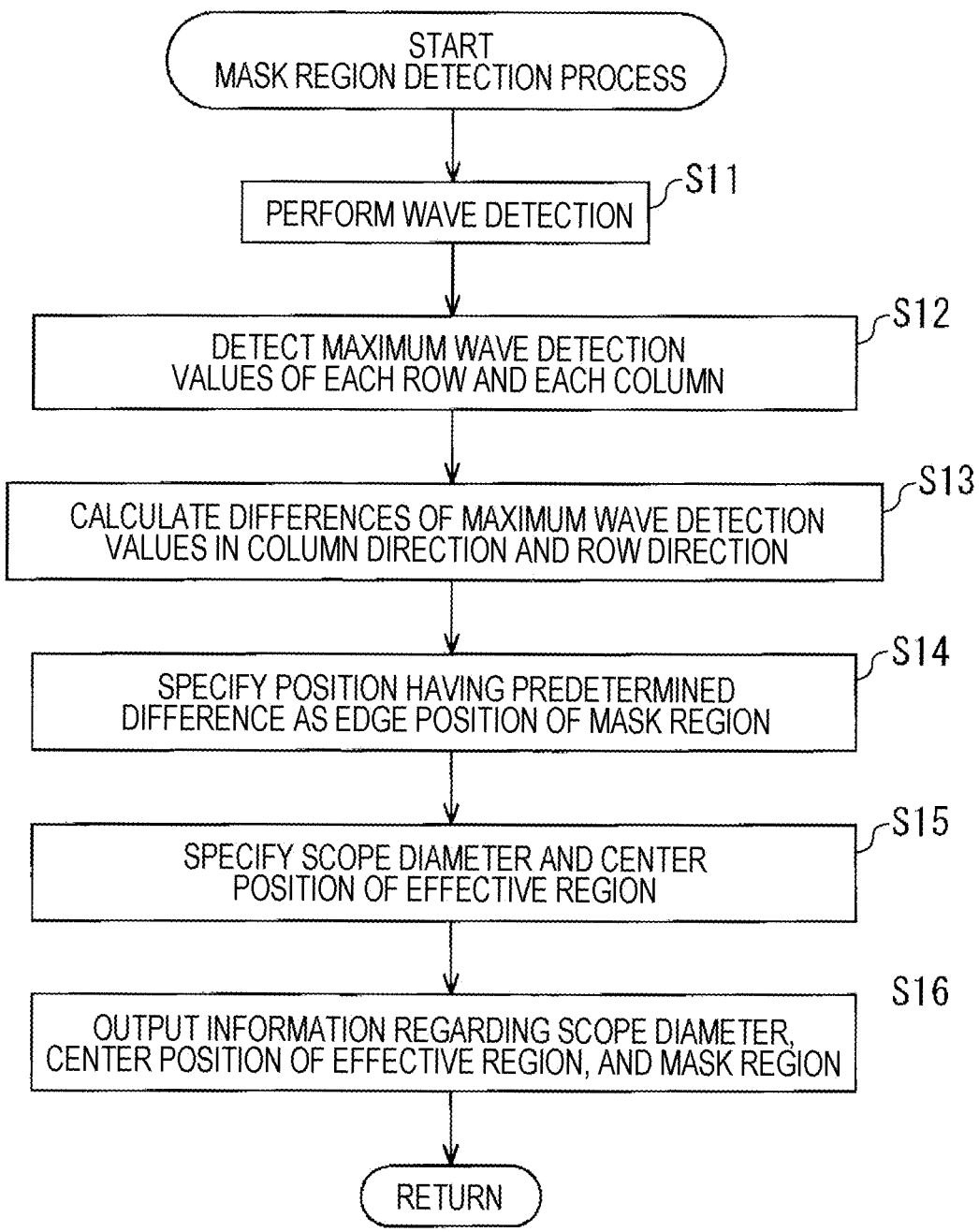
FIG. 15 is a flowchart for describing a mask region detection processing performed in step S3 of FIG. 14.

The process of FIG. 15 is to detect a mask region using the sampling value obtained by the sampling unit 133. The photographic signals of the pixels of each sampling frame set for the entire photographic image are supplied from the sampling frame gate 132 to the sampling unit 133 as described in conjunction with FIGS. 7 and 8.

In step S11, the sampling unit 133 samples the photographic signal supplied from the sampling frame gate 132 and outputs sampling values of each sampling frame.

In step S12, the mask detection unit 134 detects a maximum sampling value from sampling values of sampling frames of each column. In addition, the mask detection unit 134 detects a maximum sampling value from sampling values of sampling frames of each row.

In step S13, the mask detection unit 134 obtains differences between sampling values of every other column in an array of maximum sampling values of each column. In addition, the mask detection unit 134 obtains differences between sampling values of every other row in an array of maximum sampling values of each row.

In step S14, the mask detection unit 134 sequentially calls the differences between sampling values of every other column and detects positions where a difference equal to or larger than a threshold value is obtained as left and right edge positions of the mask region. In addition, the mask detection unit 134 sequentially calls the differences between sampling values of every other row and detects positions where a difference equal to or larger than a threshold value is obtained as upper and lower edge positions of the mask region.

In step S15, the mask detection unit 134 specifies the scope diameter and the center position of the effective region on the basis of the edge width of the effective region.

In step S16, the mask detection unit 134 outputs information regarding the scope diameter, the center position of the effective region, and the position of the mask region to the lens controller 136 as a detection result of the mask region. Then, the process returns to step S3 of FIG. 14, and the subsequent processes are performed.

Next, another mask region detection process performed in step S3 of FIG. 14 will be described with reference to the flowchart of FIG. 16.

Figure 16:
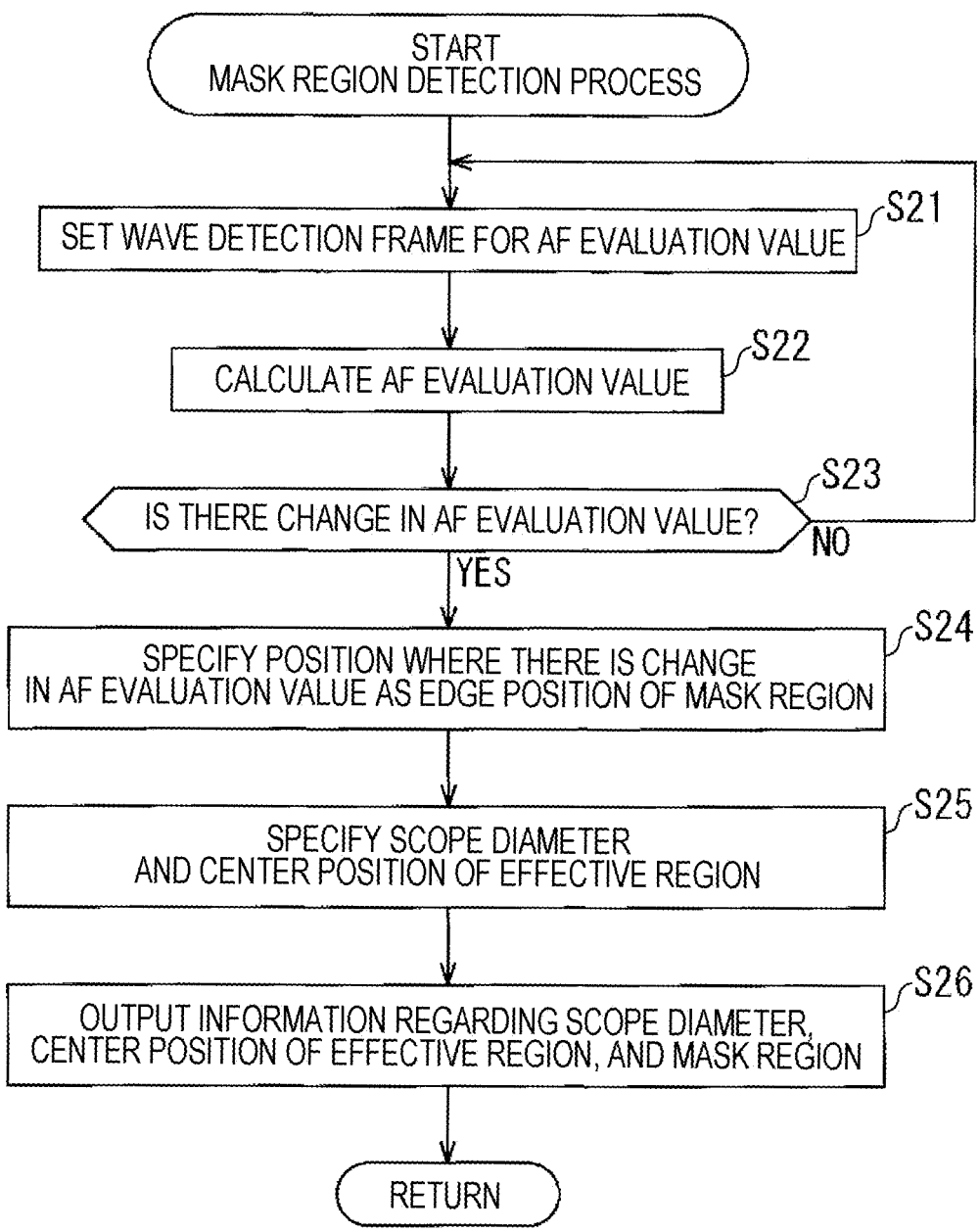
FIG. 16 is a flowchart for describing another mask region detection processing performed in step S3 of FIG. 14.

The process of FIG. 16 is a process of detecting the mask region using the AF evaluation value obtained by the AF sampling unit 135.

In step S21, the lens controller 136 outputs information regarding the positions of the sampling frames to the sampling frame gate 132 and sets the sampling frames. For example, information for setting the sampling frames in each position of the photographic image as described in conjunction with FIGS. 9, 10, and 11 is supplied from the lens controller 136 to the sampling frame gate 132. When the sampling frame is set, the photographic signal corresponding to the pixel of the sampling frame is supplied from the sampling frame gate 132 to the AF sampling unit 135.

In step S22, the AF sampling unit 135 calculates the AF evaluation value on the basis of the photographic signal supplied from the sampling frame gate 132. The calculated AF evaluation value is supplied to the mask detection unit 134.

In step S23, the mask detection unit 134 determines whether or not a change equal to or larger than a threshold value is generated in the AF evaluation value. If it is determined that a change equal to or larger than the threshold value is not generated in step S23, the process returns to step S21, and the aforementioned process is repeated after setting the sampling frame by changing the position or width.

Otherwise, if it is determined that a change equal to or larger than the threshold value is generated in the AF evaluation value in step S23, the mask detection unit 134 specifies the position where the change equal to or larger than the threshold value is generated in the AF evaluation value as the edge position of the mask region in step S24.

The process after specifying the edge position of the mask region is similar to that subsequent to step S15 in FIG. 15. Specifically, in step S25, the mask detection unit 134 specifies the scope diameter and the center position of the effective region on the basis of the edge width of the effective region.

In step S26, the mask detection unit 134 outputs information regarding the scope diameter, the center position of the effective region, and the position of the mask region to the lens controller 136 as a detection result of the mask region. Then, the process returns to step S3 of FIG. 14, and the subsequent process is performed.

Through the aforementioned processes, the CCU 12 can set the calculation target region for the AF evaluation value in an appropriate position of the effective region with a suitable size depending on the type of the scope 52 installed in the endoscope 19 which is a rigid endoscope.

In addition, the CCU 12 can suitably set parameters such as the AF speed or the wobbling amplitude depending on a specification of the scope 52 and thus improve the AF performance. Since the AF speed and the wobbling amplitude are set depending on the specification of the scope 52, it is possible to avoid degradation of image quality such as a deviation in the AF operation, a blurry stop phenomenon, and visualization of a wobbling operation.

For example, if a large diameter scope is installed, and the AF operation is performed using an F-number and a depth of focus larger than suitable values, the AF speed becomes too fast, and a deviation occurs in the AF operation. In addition, a minute vibration in the wobbling operation is visualized on the output image disadvantageously, for example.

In comparison, if a small diameter scope is installed, and the AF operation is performed using an F-number and a depth of focus smaller than suitable values, the AF speed becomes too slow, and the focusing is delayed disadvantageously. In addition, since the amplitude of the wobbling operation is short, it is difficult to obtain a focus direction, and a so-called blurry stop in which the AF operation stops in a blurry screen state occurs disadvantageously.

If the AF operation is performed using a suitable value depending on the specification of the scope, it is possible to avoid such disadvantages that may occur due to an inappropriate specification of the scope.

That is, the endoscope system 1 can provide an operator with an endoscopic image suitable for a surgical operation.

Other Examples

Application Example to AE

This embodiment is also applicable to the automatic exposure (AE) processing for performing the AE on the basis of the detection result of the mask region. The AE is performed by automatically adjusting parameters such as a shutter speed and an ISO sensitivity without an operator's manipulation.

Figure 17:
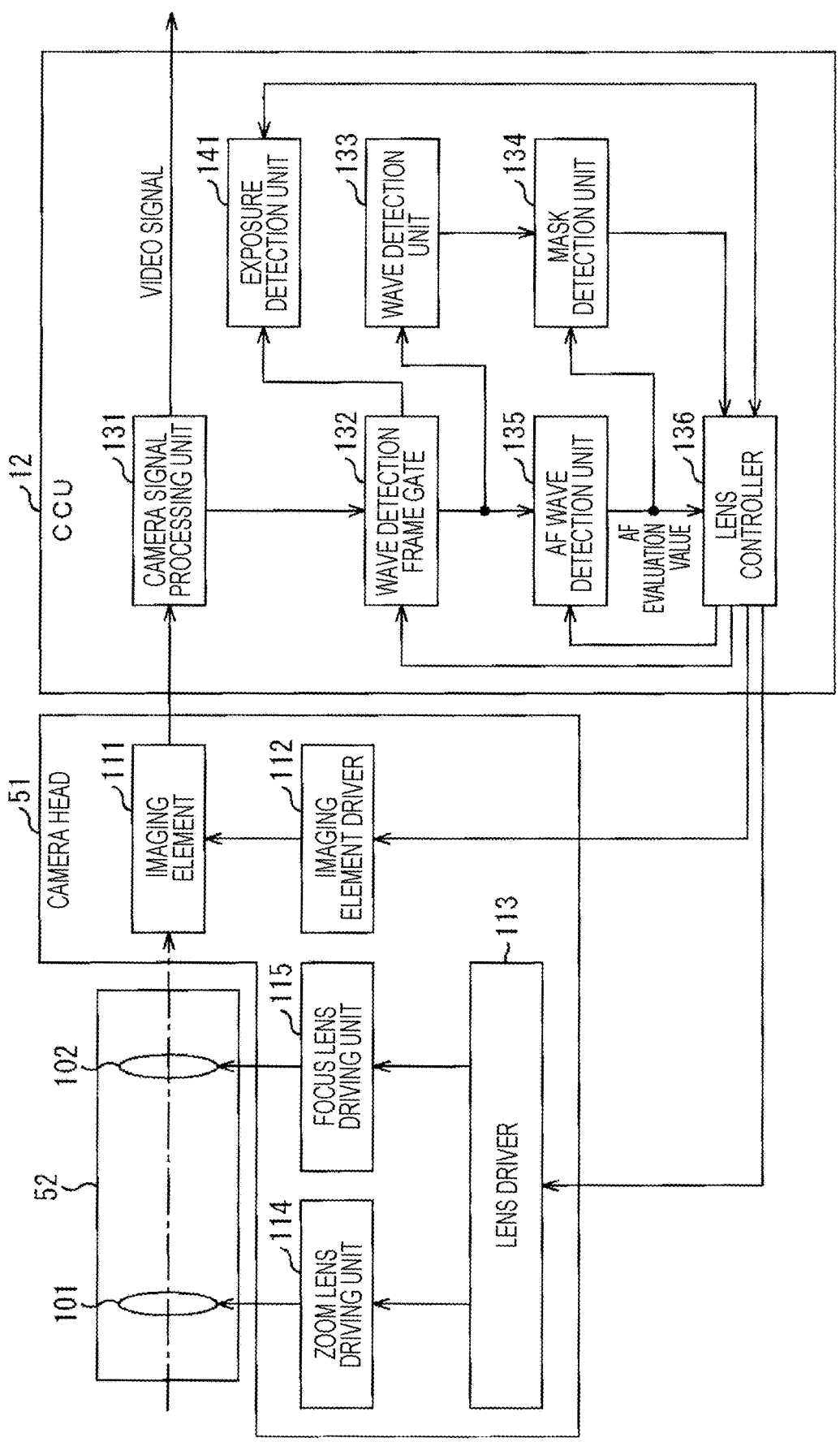
FIG. 17 is a block diagram illustrating an exemplary configuration of the CCU for an AE processing.

FIG. 17 is a block diagram illustrating an exemplary configuration of the CCU 12 for performing the AE.

In FIG. 17, like reference numerals denote like elements as in FIG. 5. Some components will not be repeatedly described. The configuration of the CCU 12 of FIG. 17 is different from that of FIG. 5 in that an exposure detection unit 141 is provided.

Out of the photographic signals supplied from the camera signal processing unit 131, the sampling frame gate 132 outputs a photographic signal of the pixel of the sampling frame used for exposure evaluation to the exposure detection unit 141.

The exposure detection unit 141 calculates the AE evaluation value as an evaluation value for exposure evaluation on the basis of the photographic signal of the pixel of the sampling frame and outputs the AE evaluation value to the lens controller 136.

The lens controller 136 outputs a control signal for adjusting the shutter speed or the ISO sensitivity to the imaging element driver 112 on the basis of the AE evaluation value calculated by the exposure detection unit 141 to perform the automatic exposure processing.

FIG. 18 is a diagram illustrating an exemplary setting of the evaluation value calculation target region for the AE evaluation value.

The setting of the evaluation value calculation target region of FIG. 18 corresponds to the setting of the evaluation value calculation target region described in conjunction with FIGS. 12A and 12B.

As illustrated in the right half of FIG. 18, the lens controller 136 sets the evaluation value calculation target region serving as a calculation target for the AE evaluation value inside the effective region so as not to overlap with the mask region. For example, the evaluation value calculation target region is set by magnifying or reducing the size of the default area and shifting the default center position on the basis of the detection result of the mask region.

The oblong rectangular area A11 illustrated in the right half of FIG. 18 is an evaluation value calculation target region set inside the effective region having a diameter shorter than the vertical length of the photographic image. In the example of FIG. 18, for example, the evaluation value calculation target region is set by reducing the default size illustrated in the left half of FIG. 18.

Information regarding such an evaluation value calculation target region is supplied from the lens controller 136 to the sampling frame gate 132, and the sampling frames serving as a calculation target of the AE evaluation value are set inside the evaluation value calculation target region.

The exposure detection unit 141 calculates the AE evaluation value on the basis of the photographic signals of the pixels of the sampling frames set inside the evaluation value calculation target region. In addition, the lens controller 136 performs the automatic exposure processing on the basis of the calculated AE evaluation value.

As a result, the CCU 12 can appropriately adjust the exposure of the surgical treatment portion imaged on the effective region.

For example, in a case where the sampling frames for exposure evaluation are set in the mask region, a control for increasing exposure is performed in the AE, and as a result, exposure may become excessive in some cases. By evaluating the exposure only using the sampling frames inside the effective region, the CCU 12 can adjust a brightness of the surgical treatment portion to suitable exposure.

FIG. 19 is a diagram illustrating another exemplary setting of the evaluation value calculation target region for the AE evaluation value.

The setting of the evaluation value calculation target region of FIG. 19 corresponds to the setting of the evaluation value calculation target region described in conjunction with FIGS. 13A and 13B.

Each segment of the mesh pattern overlapping on the photographic image of the left half of FIG. 19 represents a sampling frame. In the example of FIG. 19, a plurality of sampling frames (ten sampling frames in the vertical direction and ten frames in the horizontal direction) are set side by side in a matrix shape around the center of the photographic image. In this example, the positions of the sampling frames are fixed regardless of the range of the effective region. The photographic signals of the pixels of each sampling frame are supplied from the sampling frame gate 132 to the exposure detection unit 141.

Out of the sampling frames fixedly set in this manner, the lens controller 136 selects the sampling frames entirely included in the effective region without overlapping with the mask region as the evaluation value calculation target region serving as a calculation target for the AE evaluation value. The sampling frames colored in the right half of FIG. 19 are sampling frames selected as the evaluation value calculation target region. Meanwhile, the sampling frames overlapping with the mask region are treated as invalid sampling frames (having a weight of zero).

The lens controller 136 outputs information regarding the sampling frame selected as the evaluation value calculation target region to the exposure detection unit 141 to calculate the AE evaluation value for the sampling frame selected as the evaluation value calculation target region.

Information regarding such an evaluation value calculation target region is supplied from the lens controller 136 to the exposure detection unit 141, and the AE evaluation value is calculated on the basis of the pixel signals of the pixels of the sampling frames set as the evaluation value calculation target region. In addition, the lens controller 136 performs the automatic exposure processing on the basis of the calculated AE evaluation value.

As a result, the CCU 12 can suitably adjust exposure of the surgical treatment portion imaged on the effective region.

The automatic exposure processing may be performed in combination with the autofocus processing described above. Specifically, the control process of the lens controller 136 is a process including at least one of the automatic exposure processing or the autofocus processing.

Application Example to AWB

The white balance processing for performing an auto white balance (AWB) of the endoscope system 1 may be executed by the camera signal processing unit 131 on the basis of the detection result of the mask region.

In this case, the detection result of the mask region is supplied from the mask detection unit 134 to the camera signal processing unit 131, and the white balance processing is performed on the basis of the photographic signals of the pixels of the effective region.

The white balance processing is a process of correcting colors of the photographic image to image the surgical treatment portion with suitable color tones. For example, a photographic environment is estimated on the basis of the photographic signals (color signals) of the pixels of the effective region, and the colors generated from the photographic signals are corrected.

In addition, the white balance processing may be performed such that a color temperature of the light source is estimated from the photographic signals of the pixels of the effective region, and the colors are corrected depending on the color temperature of the light source stored in advance.

In addition, if it is determined that red light is weak inside the effective region, the white balance processing may be performed to emphasize the red light in order to highlight a blood vessel.

If the white balance processing is performed using the photographic signals of the pixels of the effective region in this manner, it is possible to obtain the photographic image on which the surgical treatment portion is imaged with appropriate color tones.

Other Examples

While a case where the AF, AE, and AWB based on the detection result of the mask region are applied to the endoscope system 1 has been described, the present technology may also be applicable to a case where the AF, AE, and AWB are performed in the microscope system.

The mask region is detected on the basis of the sampling value obtained by the sampling unit 133 or the AF evaluation value obtained by the AF sampling unit 135 in the aforementioned description. Alternatively, the mask region may be detected on the basis of both the sampling value and the AF evaluation value.

A series of processes described above may be executed using either hardware or software. In a case where a series of processes are executed using software, a program included in this software is installed from a program recording medium to a computer integrated to dedicated hardware, a general-purpose personal computer, and the like.

FIG. 20 is a block diagram illustrating an exemplary hardware configuration of the computer for executing a series of processes described above using a program.

A central processing unit (CPU) 1001, a read only memory (ROM) 1002, and a random access memory (RAM) 1003 are connected to each other via a bus 1004.

An input/output interface 1005 is further connected to the bus 1004. An input unit 1006 such as a keyboard or a mouse and an output unit 1007 such as a display or a loudspeaker are connected to the input/output interface 1005. In addition, a storage unit 1008 such as a hard disk or a non-volatile memory, a communication unit 1009 such as a network interface, and a drive 1010 for driving a removable medium 1011 are connected to the input/output interface 1005.

In the computer configured in this manner, the CPU 1001 performs a series of processes described above by loading and executing, for example, the program stored in the storage unit 1008 on the RAM 1003 via the input/output interface 1005 and the bus 1004.

The program executed by the CPU 1001 is recorded, for example, on the removable medium 1011 or is provided via a wired or wireless transmission medium such as a local area network, the Internet, and digital broadcasting, and is installed in the storage unit 1008.

Note that the program executed by the computer may be a program processed in a time-series manner depending on the sequence described herein or a program processed in parallel or at necessary timings such as in response to a call.

Note that, herein, a system refers to a set of a plurality of constituent elements (devices, modules (components), or the like) regardless of whether or not all of them are integrated into the same casing. Therefore, the system encompasses a plurality of devices housed in separate casings and connected via a network, a single device having a plurality of modules housed in a single casing, and the like.

Note that the advantageous effects described herein are just for exemplary purposes and are not construed in a limitative sense. Another advantageous effect may also be included.

Embodiments of the present technology are not limited to those described above, and various changes or modifications may be possible without departing from the scope and spirit of the present technology.

For example, the present technology may be applicable to a cloud computing environment in which a single function is processed in a distributed and cooperated manner across a plurality of devices connected via a network.

In addition, each step of the flowchart described above may be executed using a single device or using a plurality of devices in a distributed manner.

In addition, in a case where a plurality of processes are included in a single step, they may be executed using a single device or using a plurality of devices in a distributed manner.

<Combination of Configurations>

The present technology may also include the following configurations.

(1) According to one aspect, a system includes an endoscope including a scope and an image sensor, the image sensor being configured to capture medical image data that includes effective image portion data and a mechanical vignetting portion data, the mechanical vignetting portion data of the medical image data being generated due to mechanical vignetting caused by a difference in the image sensor which generates the medical image data and the scope; and circuitry configured to determine evaluation information from image data which is from the effective image portion data, and execute a control process to at least partially control at least one of an autofocus processing, and an auto white balance processing on the endoscope on the basis of the evaluation information.

(2) The system according to (1), wherein the determining by the circuitry of the evaluation information determines the evaluation information from only the medical image data which is from the effective image portion data.

(3) The system according to (2), wherein the difference is due to a different shape of the image sensor and a light passed through the scope.

(4) The system according to (3), wherein the image sensor is rectangular and the effective image portion data is of circular image.

(5) The system according to (2), wherein the difference is due a different size of the image sensor and the scope.

(6) The system according to (5), wherein an image from the scope which is used to generate the effective image portion data exceeds a size of an effective area of the image sensor in a first dimension of the image sensor, is smaller than a size of the effective area of the image sensor in a second dimension of the image sensor which is perpendicular to the first dimension, and the first dimension and the second dimension are both in an imaging sensing plane of the image sensor.

(7) The system according to (2), further including a light which illuminates a target which corresponds to the effective image portion data.

(8) The system according to (2), further including a lens system, wherein the executing of the control process by the circuitry generates information to focus the lens system on the basis of the evaluation information.

(9) The system according to (2), wherein the executing of the control process by the circuitry generates white balance information to set a white balance of the medical image.

(10) The system according to (1), wherein the circuitry is further configured to sample luminance signals from the image sensor, and determine where the effective image portion data exists and the effective image portion data using the luminance signals.

(11) The system according to (10), wherein the determining of where the effective image portion data exists detects an edge of the effective image portion data on the basis of the luminance signals which have been sampled and are in a matrix shape, and specifies a diameter of the scope and a center position of the effective image portion data.

(12) The system according to (1), wherein the circuitry is further configured to perform sampling in sampling frames set on the medical image data to obtain the evaluation information which is used for the autofocus processing, and determine where the effective image portion data exists and the effective image portion data using the evaluation information which is used for the autofocus processing, wherein the executing of the control process at least partially controls the autofocus processing based on the evaluation information.

(13) The system according to (12), wherein the performing of the sampling in sampling frames changes at least one of a position and a size of the sampling frames.

(14) The system according to (12), wherein the determining of where the effective image portion data exists specifies a diameter of the scope and a center position of the effective image portion data.

(15) The system according to (1), wherein the circuitry is further configured to set an evaluation value calculation target region used as the effective image portion using a diameter of the scope and a center position of the effective image portion data.

(16) The system according to (1), wherein the executing of the control process executes the control process on the basis of the evaluation information which is determined based on the effective image portion data indicated by a diameter of the scope and a center position of the effective image portion data out of evaluation value calculation target regions set in a matrix shape on the medical image data as a calculation target for the evaluation information.

(17) The system according to (1), wherein the determining of the evaluation information determines information used for the autofocus processing on the basis of at least one of an F-number or a depth of focus of the scope estimated using the image data from the effective image portion data.

(18) The system according to (1), wherein the executing of the control process references a table containing at least one of an F-number or a depth of focus of the scope stored in advance on the basis of a determining result of the determining of the evaluation information and sets a parameter for defining the autofocus processing on the basis of a result of the referencing.

(19) A system for processing medical images, including circuitry configured to obtain medical image data by an endoscope including an imager head and a scope attached to the imager head, determine evaluation information using effective image area data of the medical image data without using mechanical vignetting area data of the medical image data, the effective area of the medical image data being generated due to mechanical vignetting caused by the scope, and execute a control process including at least one of an autofocus process and an auto white balance process on the basis of the evaluation information.

(20) The system according to (19) further including the imager head which includes an image sensor; and the scope which is a medical instrument, wherein the mechanical vignetting area data is due to a different shape of the image sensor and the scope.

(21) The system according to (20) wherein the image sensor is rectangular and the medical image data produced by the scope is of a circular image.

(22) The system according to (19), further including the imager head which includes an image sensor; and the scope which is a medical instrument, wherein the mechanical vignetting area data is due to a different size of the image sensor and the scope.

(23) The system according to (22), wherein a medical image produced by the endoscope exceeds a size of the image sensor in a first dimension of the image sensor, is smaller than a size of the image sensor in a second dimension of the image sensor which is perpendicular to the first dimension, and the first dimension and the second dimension are both in an imaging sensing plane of the image sensor.

(24) The system according to (19), further including a light which illuminates a target which corresponds to the medical image data.

(25) The system according to (19) further including a lens system attached to the scope, wherein the circuitry configured to execute the control process generates information to focus the lens system on the basis of the evaluation information.

(26) The system according to (19), wherein the circuitry configured to execute the control process generates white balance information to set a white balance of the medical image.

(27) A method of processing medical image information including determining evaluation information using effective image portion data of medical image data, the medical image data including the effective image portion data and mechanical vignetting portion data, the mechanical vignetting portion data of the medical image data being generated due to mechanical vignetting caused by a difference in an image sensor which generates the medical image data and a medical instrument, executing a control process including at least one of an autofocus process, or an auto white balance process on the basis of the evaluation information.

(28) The method according to (27), wherein the determining of the evaluation information determines the evaluation information from only the effective image portion data of the medical image data without using the mechanical vignetting portion data.

(29) The method according to (28), further including generating the medical image data using the image sensor and the medical instrument, wherein the difference is due a different shape of the image sensor and the medical instrument.

(30) The method according to (29), wherein the image sensor is rectangular, and an image corresponding to the effective image portion data produced by the medical instrument is circular.

(31) The method according to (28), further including generating the medical image data using the image sensor and the medical instrument, wherein the difference is due a different size of the image sensor and the medical instrument.

(32) The method according to (31), wherein an image from the medical instrument which is used to generate the effective image portion data exceeds a size of the image sensor in a first dimension of the image sensor, is smaller than a size of the image produced by the medical instrument in a second dimension of the image sensor which is perpendicular to the first dimension, and the first dimension and the second dimension are both in an imaging sensing plane of the image sensor.

(33) The method according to (28), wherein the medical instrument includes a scope.

(34) The method according to (28), further including generating the medical image data using the image sensor and the medical instrument which includes a scope.

(35) The method according to (34), further including illuminating, using a light, a target which corresponds to the medical image.

(36) The method according to (27), wherein the executing of the control process executes a focusing of a lens system using the evaluation information.

(37) The method according to (27), wherein the executing of the control process executes the auto white balance process using the evaluation information.

(38) The method according to claim (27), further including sampling luminance signals from the image sensor, and determining where the effective image portion data exists and the effective image portion data using the luminance signals.

(39) The method according to (38), wherein the determining of where the effective image portion data exists detects an edge of the effective image portion data on the basis of the luminance signals which have been sampled and are in a matrix shape, and specifies a diameter of the scope and a center position of the effective image portion data.

(40) The method according to (27), further including performing sampling in sampling frames set on the medical image data to obtain the evaluation information which is used for the autofocus processing, and determining where the effective image portion data exists and the effective image portion data using the evaluation information which is used for the autofocus process, wherein the executing of the control process at least partially controls the autofocus process based on the evaluation information.

(41) The method according to (40), wherein:
the performing of the sampling in sampling frames changes at least one of a position and a size of the sampling frames.

(42) The method according to (40), wherein:
the determining of where the effective image portion data exists specifies a diameter of the scope and a center position of the effective image portion data.

(43) The method according to (27), further comprising:
setting an evaluation value calculation target region used as the effective image portion using a diameter of the scope and a center position of the effective image portion data.

(44) The method according to (27), wherein the executing of the control process executes the control process on the basis of the evaluation information which is determined based on the effective image portion data indicated by a diameter of the scope and a center position of the effective image portion data out of evaluation value calculation target regions set in a matrix shape on the medical image data as a calculation target for the evaluation information.

(45) The method according to (27), wherein the determining of the evaluation information determines information used for the autofocus processing on the basis of at least one of an F-number or a depth of focus of the scope estimated using the image data from the effective image portion data.

(46) The method according to (27), wherein the executing of the control process references a table containing at least one of an F-number or a depth of focus of the scope stored in advance on the basis of a determining result of the determining of the evaluation information and sets a parameter for defining the autofocus processing on the basis of a result of the referencing.

<Combination of Configurations>

The present technology may also include the following configurations.

(1)

An endoscope system including:

a light source device configured to irradiate light onto a surgical field area;

an image sensing device configured to photograph the surgical field area using a detachably installed scope; and an information processing device connected to the image sensing device and the light source device and provided with a detection unit configured to detect an effective region of the scope from a photographic image photographed by the image sensing device, and a control unit configured to execute a control process including at least one of an autofocus processing, an automatic exposure processing, or an auto white balance processing on the basis of an evaluation value of the effective region.

(2)

The endoscope system according to (1), in which the effective region has no vignetting caused by the scope.

(3)

The endoscope system according to (1) or (2), further including a first sampling unit configured to sample luminance signals of each region set in the photographic image, in which the detection unit detects the effective region on the basis of sampling values of each region of the photographic image.

(4)

The endoscope system according to (3), in which the detection unit detects an edge of the effective region on the basis of the sampling value of each region set in a matrix shape on the photographic image and specifies a diameter of the scope and a center position of the effective region.

(5)

The endoscope system according to (1), further including a second sampling unit configured to perform sampling in sampling frames set on the photographic image and calculate an evaluation value for the autofocus processing, in which the detection unit detects the effective region on the basis of the evaluation value for the autofocus processing, and the control unit executes the autofocus processing as the control process on the basis of the evaluation value for the autofocus processing.

(6)

The endoscope system according to (5), in which the second sampling unit calculates the evaluation value for the autofocus processing used in detection of the effective region by changing at least one of a position or a size of the sampling frame.

(7)

The endoscope system according to (6), in which the detection unit detects an edge of the effective region on the basis of the evaluation value for the autofocus processing and specifies the diameter of the scope and the center position of the effective region.

(8)

The endoscope system according to any of (1) to (7), in which the control unit sets an evaluation value calculation target region serving as a calculation target for the evaluation value in the effective region indicated by the diameter of the scope and the center position of the effective region.

(9)

The endoscope system according to any of (1) to (8), in which the control unit executes the control process on the basis of the evaluation value calculated for the evaluation value calculation target region of the effective region indicated by the diameter of the scope and the center position of the effective region out of the evaluation value calculation target regions set in a matrix shape on the photographic image as a calculation target for the evaluation value.

(10)

The endoscope system according to any of (1) to (9), in which the control unit sets a parameter for defining the autofocus processing on the basis of at least one of an F-number or a depth of focus of the scope estimated on the basis of a detection result of the detection unit.

(11)

The endoscope system according to any of (1) to (9), in which the control unit references a table containing at least one of an F-number or a depth of focus of the scope stored in advance on the basis of a detection result of the detection unit and sets a parameter for defining the autofocus processing on the basis of a result of the referencing.

(12)

A method of controlling an endoscope system, the method including:

irradiating light onto a surgical field area using a light source device;

photographing the surgical field area through a detachably installed scope using an image sensing device; and using an information processing device connected to the image sensing device and the light source device to detect an effective region of the scope from a photographic image photographed by the image sensing device and execute a control process including at least one of an autofocus processing, an automatic exposure processing, or an auto white balance processing on the basis of an evaluation value of the effective region.

(13)

An information processing device of an endoscope system, the information processing device being connected to a light source device configured to irradiate light onto a surgical field area and an image sensing device configured to photograph the surgical field area through a detachably installed scope, the information processing device including:

a detection unit configured to detect an effective region of the scope from a photographic image photographed by the image sensing device; and a control unit configured to execute a control process including at least one of an autofocus processing, an automatic exposure processing, or an auto white balance processing on the basis of an evaluation value of the effective region.

(14)

A program for causing a computer serving as an information processing device of an endoscope system to execute a processing, the information processing device being connected to a light source device configured to irradiate light onto a surgical field area and an image sensing device configured to photograph the surgical field area through a detachably installed scope, the processing including:

detecting an effective region of the scope from a photographic image photographed by the image sensing device; and executing a control process including at least one of an autofocus processing, an automatic exposure processing, or an auto white balance processing on the basis of an evaluation value of the effective region.

REFERENCE SIGNS LIST

1 Endoscope system
12 CCU
19 Endoscope
51 Camera head
52 Scope
111 Imaging element
112 Imaging element driver
113 Lens driver
114 Zoom lens driving unit
115 Focus lens driving unit
131 Camera signal processing unit
132 Sampling frame gate
133 Sampling unit
134 Mask detection unit
135 AF sampling unit
136 Lens controller
141 Exposure detection unit

The invention claimed is:

1. A system, comprising:
an endoscope including a scope and an image sensor, the image sensor being configured to capture medical image data that includes effective image portion data and a mechanical vignetting portion data, the mechanical vignetting portion data of the medical image data being generated due to mechanical vignetting caused by a difference in the image sensor which generates the medical image data and the scope; and
circuitry configured to
determine evaluation information from image data which is only from the effective image portion data of the medical image data without using the mechanical vignetting portion data, and
execute a control process to at least partially control at least one of an autofocus processing, and an auto white balance processing on the endoscope on the basis of the evaluation information.

2. The system according to claim 1, wherein:
the difference is due to a different shape of the image sensor and a light passed through the scope.

3. The system according to claim 2, wherein:
the image sensor is rectangular and the effective image portion data is of circular image.

4. The system according to claim 1, wherein:
the difference is due a different size of the image sensor and the scope.

5. The system according to claim 4, wherein:
an image from the scope which is used to generate the effective image portion data exceeds a size of an effective area of the image sensor in a first dimension of the image sensor, is smaller than a size of the effective area of the image sensor in a second dimension of the image sensor which is perpendicular to the first dimension, and the first dimension and the second dimension are both in an imaging sensing plane of the image sensor.

6. The system according to claim 1, further comprising:
a light which illuminates a target which corresponds to the effective image portion data.

7. The system according to claim 1, further comprising:
a lens system,
wherein the executing of the control process by the circuitry generates information to focus the lens system on the basis of the evaluation information.

8. The system according to claim 1, wherein:
the executing of the control process by the circuitry generates white balance information to set a white balance of the medical image.

9. The system according to claim 1, wherein the circuitry is further configured to:
sample luminance signals from the image sensor, and
determine where the effective image portion data exists and the effective image portion data using the luminance signals.

10. The system according to claim 9, wherein the determining of where the effective image portion data exists detects an edge of the effective image portion data on the basis of the luminance signals which have been sampled and are in a matrix shape, and specifies a diameter of the scope and a center position of the effective image portion data.

11. The system according to claim 1, wherein the circuitry is further configured to:
perform sampling in sampling frames set on the medical image data to obtain the evaluation information which is used for the autofocus processing, and
determine where the effective image portion data exists and the effective image portion data using the evaluation information which is used for the autofocus processing,
wherein the executing of the control process at least partially controls the autofocus processing based on the evaluation information.

12. The system according to claim 11, wherein:
the performing of the sampling in sampling frames changes at least one of a position and a size of the sampling frames.

13. The system according to claim 11, wherein:
the determining of where the effective image portion data exists specifies a diameter of the scope and a center position of the effective image portion data.

14. The system according to claim 1, wherein the circuitry is further configured to:
set an evaluation value calculation target region used as the effective image portion using a diameter of the scope and a center position of the effective image portion data.

15. The system according to claim 1, wherein:
the executing of the control process executes the control process on the basis of the evaluation information which is determined based on the effective image portion data indicated by a diameter of the scope and a center position of the effective image portion data out of evaluation value calculation target regions set in a matrix shape on the medical image data as a calculation target for the evaluation information.

16. The system according to claim 1, wherein:
the determining of the evaluation information determines information used for the autofocus processing on the basis of at least one of an F-number or a depth of focus of the scope estimated using the image data from the effective image portion data.

17. The system according to claim 1, wherein:
the executing of the control process references a table containing at least one of an F-number or a depth of focus of the scope stored in advance on the basis of a determining result of the determining of the evaluation information and sets a parameter for defining the autofocus processing on the basis of a result of the referencing.

18. A system for processing medical images, comprising:
circuitry configured to
- obtain medical image data by an endoscope including an imager head and a scope attached to the imager head,
- determine evaluation information using only effective image area data of the medical image data without using mechanical vignetting area data of the medical image data, the mechanical vignetting area data of the medical image data being generated due to mechanical vignetting caused by the scope, and
- execute a control process including at least one of an autofocus process and an auto white balance process on the basis of the evaluation information.

19. The system according to claim 18, further comprising:
the imager head which includes an image sensor; and
the scope which is a medical instrument,
wherein the mechanical vignetting area data is due to a different shape of the image sensor and the scope.

20. The system according to claim 19, wherein:
the image sensor is rectangular and the medical image data produced by the scope is of a circular image.

21. The system according to claim 18, further comprising:
the imager head which includes an image sensor; and
the scope which is a medical instrument,
wherein the mechanical vignetting area data is due to a different size of the image sensor and the scope.

22. The system according to claim 21, wherein:
a medical image produced by the endoscope exceeds a size of the image sensor in a first dimension of the image sensor, is smaller than a size of the image sensor in a second dimension of the image sensor which is perpendicular to the first dimension, and the first dimension and the second dimension are both in an imaging sensing plane of the image sensor.

23. The system according to claim 18, further comprising:
a lens system attached to the scope,
wherein the circuitry configured to execute the control process generates information to focus the lens system on the basis of the evaluation information.

24. The system according to claim 18, wherein:
the circuitry configured to execute the control process generates white balance information to set a white balance of the medical image.

25. A method of processing medical image information, comprising:
- determining evaluation information using only effective image portion data of medical image data, the medical image data including the effective image portion data and mechanical vignetting portion data, the mechanical vignetting portion data of the medical image data being generated due to mechanical vignetting caused by a difference in an image sensor which generates the medical image data and a medical instrument; and
- executing a control process including at least one of an autofocus process, or an auto white balance process on the basis of the evaluation information.

26. The method according to claim 25, further comprising:
generating the medical image data using the image sensor and the medical instrument,
wherein the difference is due a different shape of the image sensor and the medical instrument.

27. The method according to claim 25, further comprising:
generating the medical image data using the image sensor and the medical instrument,
wherein the difference is due a different size of the image sensor and the medical instrument.

28. The method according to claim 27, wherein:
an image from the medical instrument which is used to generate the effective image portion data exceeds a size of the image sensor in a first dimension of the image sensor, is smaller than a size of the image produced by the medical instrument in a second dimension of the image sensor which is perpendicular to the first dimension, and the first dimension and the second dimension are both in an imaging sensing plane of the image sensor.

* * * * *